US012201608B2

(12) United States Patent
Nahama et al.

(10) Patent No.: US 12,201,608 B2
(45) Date of Patent: Jan. 21, 2025

(54) METHODS FOR TREATING PARKINSON'S DISEASE BY ADMINISTERING RESINIFERATOXIN

(71) Applicant: Sorrento Therapeutics, Inc., San Diego, CA (US)

(72) Inventors: Alexis Nahama, San Diego, CA (US); Henry Hongjun Ji, Rancho Santa Fe, CA (US)

(73) Assignee: Vivasor, Inc., San Diego, CA (US)

( * ) Notice: Subject to any disclaimer, the term of this patent is extended or adjusted under 35 U.S.C. 154(b) by 784 days.

(21) Appl. No.: 17/345,641

(22) Filed: Jun. 11, 2021

(65) Prior Publication Data

US 2021/0299090 A1 Sep. 30, 2021

Related U.S. Application Data

(63) Continuation of application No. PCT/US2019/068235, filed on Dec. 23, 2019.

(60) Provisional application No. 62/914,170, filed on Oct. 11, 2019, provisional application No. 62/784,650, filed on Dec. 24, 2018.

(51) Int. Cl.

*A61K 31/357* (2006.01)
*A61K 9/00* (2006.01)
*A61P 25/16* (2006.01)

(52) U.S. Cl.

CPC .......... *A61K 31/357* (2013.01); *A61K 9/0019* (2013.01); *A61P 25/16* (2018.01)

(58) Field of Classification Search

CPC .................................................... A61K 31/357

See application file for complete search history.

(56) References Cited

U.S. PATENT DOCUMENTS 4,939,194 A 7/1990 Scott et al.
5,021,450 A 6/1991 Blumberg
5,232,684 A 8/1993 Blumberg et al.
9,956,166 B2 * 5/2018 Zucker ................. A61K 9/0085
11,679,075 B2 * 6/2023 Zucker ................. A61K 9/0019 514/185

FOREIGN PATENT DOCUMENTS

WO 2008109026 A1 9/2008

OTHER PUBLICATIONS

Brown "Resiniferatoxin: The Evolution of the 'Molecular Scalpel' for Chronic Pain Relief," Pharmaceuticals (Basel), 9 (3), pii E47 (2016).
Caterina et al. "The capsaicin receptor: a heat-activated ion channel in the pain pathway," Nature 389: 816-824 (1997).
Jellinger, "Cell death mechanisms in Parkinson's disease" J. Neural. Transm. 107: 1-29 (2000).
Karai et al. "Deletion of vanilloid receptor 1-expressing primary afferent neurons for pain control" Journal of Clinical Investigation, 113(9): 1344-1352 (2004).
Nadeau, "Parkinson's Disease" Journal of the American Geriatrics Society, 45(2): 233-240 (1997).
Nam et al. "TRPVI on astrocytes recues nigral dopamine neurons in Parkinson's disease via Cntf," Brain, 138: 3610-3622 (2015).
PCT, International Search Report and Written Opinion for PCT/US2019/068235 dated Mar. 9, 2020, p. 1-8.
Playfer, "Parkinson's Disease" Postgrad. Med. J., 73: 257-264 (1997).
Szallasi et al. "Resiniferatoxin-type phorboid vanilloids display capsaicin-like selectivity at native vanilloid receptors on rat DRG neurons and at the cloned vanilloid receptor VR1," British Journal of Pharmacology, 128: 428-434 (1999).
Szallasi et al. "The Cloned Rat Vanilloid Receptor VR1 Mediates Both R-Type Binding and C-Type Calcium Response in Dorsal Root Ganglion Neurons" Molecular Pharmacology, 56(3): 581-587 (1999).
Tominaga et al. "The Cloned Capsaicin Receptor Integrates Multiple Pain-Producing Stimuli," Neuron, 21: 531-543 (1998).
EP, Extended European Search Report corresponding to European Patent Application No. 19904905.7, mailed Jul. 27, 2022, 8 pages.
Kissin Igor et al., "Therapeutic Targeting of TRPVI by Resiniferatoxin, from Preclinical Studies to Clinical Trials", Current Topics in Medicinal Chemistry, vol. 11, No. 17, pp. 2159-2170 (2011).
Kuo et al: "Effectiveness of Intravesical Resiniferatoxin For Anticholinergic Treatment Refractory Detrusor Overactivity Due To Nonspinal Cord Lesions", Journal of Urology, vol. 170, No. 3, pp. 835-839 (2003).
Zhao ZhenXiang et al., "Capsaicin Protects Against Oxidative Insults and Alleviates Behavioral Deficits in Rats with 6-OHDA-Induced Parkinson's Disease via Activation of TRPVI", Neurochemical Research, vol. 42, No. 12, pp. 3431-3438 (2017).

* cited by examiner

*Primary Examiner* — Golam M Shameem
(74) *Attorney, Agent, or Firm* — McNeill PLLC

(57) ABSTRACT

There is disclosed a method for treating Parkinson's Disease (PD) comprising administering an effective amount of Resiniferatoxin (RTX) by an intrathecal or intracisternal administration. In some embodiments, the dose of RTX for an adult human is from about 0.1 μg to about 100 μg.

11 Claims, 13 Drawing Sheets

METHODS FOR TREATING PARKINSON'S DISEASE BY ADMINISTERING RESINIFERATOXIN

This application is a continuation of International Application No. PCT/US2019/068235, filed Dec. 23, 2019, which claims the benefit of priority of U.S. Provisional Application No. 62/784,650, filed Dec. 24, 2018, and U.S. Provisional Application No. 62/914,170, filed Oct. 11, 2019, the contents of each of which are incorporated by reference herein in their entirety.

TECHNICAL FIELD

The present disclosure provides a method for treating Parkinson's Disease (PD) comprising administering an effective amount of Resiniferatoxin (RTX) by an intrathecal or an intracisternal administration.

INTRODUCTION AND SUMMARY

RTX acts as an ultrapotent analog of capsaicin, the pungent principal ingredient of the red pepper. RTX is a tricyclic diterpene isolated from certain species of *Euphorbia*. A homovanillyl group is an important structural feature of capsaicin and is the most prominent feature distinguishing resiniferatoxin from typical phorbol-related compounds. Native RTX has the following structure:

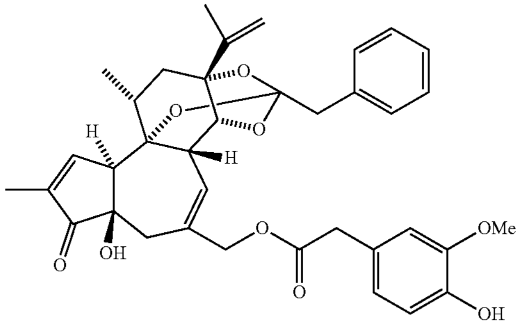 [SMILES: C=C(C)[C@]12C[C@@H](C)[C@@]34OC(Cc5ccccc5)(O[C@@H]1[C@@H]3C=C(COC(=O)Cc1ccc(O)c(OC)c1)C[C@]1(O)C(=O)C(C)=C[C@@H]41)O2]

RTX and analog compounds such as tinyatoxin and other compounds (20-homovanillyl esters of diterpenes such as 12-deoxyphorbol 13-phenylacetate 20-homovanillate and mezerein 20-homovanillate) are described in U.S. Pat. Nos. 4,939,194; 5,021,450; and 5,232,684. Other resiniferatoxin-type phorboid vanilloids have also been identified (Szallasi et al. (1999) *Brit. J. Pharmacol.* 128:428-434).

RTX is known as a TrpV1 agonist. TrpV1, the transient receptor potential cation channel subfamily V member 1 (also known as Vanilloid receptor-1 (VR1)) is a multimeric cation channel prominently expressed in nociceptive primary afferent neurons (Caterina et al. (1997) *Nature* 389:816-824; Tominaga et al. (1998) *Neuron* 21:531-543). Activation of TrpV1 typically occurs at the nerve endings via application of painful heat and is up regulated during certain types of inflammatory stimuli. Activation of TrpV1 in peripheral tissues by a chemical agonist results in the opening of calcium channels and the transduction of a pain sensation (Szalllasi et al. (1999) *Mol. Pharmacol.* 56:581-587). However, direct application of certain TrpV1 agonists to the cell body of a neuron (ganglion) expressing TrpV1 opens calcium channels and triggers a cascade of events leading to programmed cell death ("apoptosis") (Karai et al. (2004) *J. of Clin. Invest.* 113:1344-1352).

Parkinson's disease is a movement disorder of increasing occurrence in aging populations. Parkinson's disease is a common disabling disease of old age affecting about one percent of the population over the age of 60 in the United States. The incidence of Parkinson's disease increases with age and the cumulative lifetime risk of an individual developing the disease is about 1 in 40. Symptoms include pronounced tremor of the extremities, bradykinesia, rigidity and postural change. A perceived pathophysiological cause of Parkinson's disease is progressive destruction of dopamine producing cells in the basal ganglia which comprise the pars compartum of the substantia nigra, a basal nuclei located in the brain stem. Loss of dopamineric neurons results in a relative excess of acetylcholine. Jellinger, *J. Neural. Transm.* 56 (Supp); 1-29:1999.

Parkinson's disease is a progressive disorder which can begin with mild limb stiffness and infrequent tremors and progress over a period of ten or more years to frequent tremors and memory impairment, to uncontrollable tremors and dementia.

Drugs used to treat Parkinson's disease include L-dopa, selegiline, apomorphine and anticholinergics. L-dopa (levo-dihydroxy-phenylalanine) (sinemet) is a dopamine precursor which can cross the blood-brain barrier and be converted to dopamine in the brain. Unfortunately, L-dopa has a short half life in the body and it is typical after long use (i.e. after about 4-5 years) for the effect of L-dopa to become sporadic and unpredictable, resulting in fluctuations in motor function, dyskinesias and psychiatric side effects. Additionally, L-dopa can cause B vitamin deficiencies to arise.

Selegiline (Deprenyl, Eldepryl) has been used as an alternative to L-dopa, and acts by reducing the breakdown of dopamine in the brain. Unfortunately, Selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects.

Systemically administered anticholinergic drugs (such as benzhexol and orphenedrine) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth and urine retention. (Playfer, *Postgrad. Med. J.,* 73; 257-264:1997 and Nadeau, *J. Am. Ger. Soc.,* 45; 233-240:1997.

Before the introduction of L-dopa in 1969, stereotactic surgery offered one of the few treatments for Parkinson's disease. Unilateral stereotactic thalamotomy can be effective for controlling contralateral tremor and rigidity but carries a risk of hemiparesis. Bilateral thalamotomy carries an increased risk of speech and swallowing disorders resulting. Stereotactic pallidotomy, surgical ablation of part of the globus pallidus (a basal ganglia), has also be used with some success. Aside from surgical resection, high frequency stimulating electrodes placed in the ventral intermedialis nucleus has been found to suppress abnormal movements in some cases. A variety of techniques exist to permit precise location of a probe, including computed tomography and magnetic resonance imaging. Unfortunately, the akinesia, speech and gait disorder symptoms of Parkinson's disease are little helped by these surgical procedures, all of which result in destructive brain lesions.

Intracranial lesions for the treatment of tremor and other parkinsonian symptoms have been made to the globus pallidus and the ansa lenticularis. Long term results of pallidotomy have sometimes been disappointing. Positive results for the surgical arrest of tremor have been obtained by lesioning the following thalamic nuclei: (1) the ventrointermedius (Vim) or ventral lateral posterior (VLp) nucleus; (2) ventrooralis anterior (Voa) nucleus (Voa and Vop have been collectively termed the ventral lateral anterior nucleus (VLa)); (3) ventrooralis posterior (Vop) nucleus; (4) subthalamic nuclei (campotomy), and; (5) CM-Pf thalamic nuclei. Generally, the ventrolateral thalamus has been the surgical target of choice in the treatment of Parkinson's disease and other systemically administered, drug resistant tremors. Thalamic excitation of the cortex is necessary for almost all cortical activity.

Stereotactic surgery (assisted by neuroimaging and electrophysiologic recordings) has been used in the management of advanced, pharmacoresistant Parkinson's disease, targeting hyperactive globus pallidus and subthalamic nuclei. An electrode or a probe is placed into the brain using a brain atlas for reference with assistance from brain imaging by computer tomography or magnetic resonance imaging. Lesions in different parts of the *pallidum* (i.e. posteroventral *pallidum*), basal ganglia, thalamus and subthalamic nuclei have been carried out to treat motor disorders of Parkinson's disease. Unfortunately, surgical brain lesions create a risk of impairment to speech, visual and cognitive brain areas. Aside from surgical ablation or stimulation, external radiotherapy (Gamma Knife Radiosurgery) has also been used to a limited extent for the treatment of drug resistant parkinsonian tremors. Drawbacks with this procedure are that the reduction in tremor is delayed by between one week and eight months after the radiosurgery, and that long term benefits as well as radiation side effects are currently unknown.

Therefore, there is a need in the art for an improved treatment for Parkinson's Disease.

The present disclosure provides a method for treating Parkinson's Disease (PD) comprising administering an effective amount of Resiniferatoxin (RTX) by an intrathecal or an intracisternal administration. In some embodiments, the dose of RTX for an adult human is from about 0.1 μg to about 100 μg.

Embodiment 1 is a method for treating Parkinson's Disease (PD) comprising administering to a subject in need of treatment for PD an effective amount of Resiniferatoxin (RTX) intrathecally or intracisternally.

Embodiment 2 is a composition comprising resiniferatoxin (RTX) for use in a method of treating a subject in need of treatment for Parkinson's Disease (PD).

Embodiment 3 is the composition for use of embodiment 2, wherein the method comprises administering the composition to the subject intrathecally or intracisternally.

Embodiment 4 is the method of embodiment 1 or composition for use of embodiments 2 or 3, wherein the subject is an adult human.

Embodiment 5 is the method or composition for use of any one of the preceding embodiments, wherein the RTX is administered in a dose of from about 0.1 μg to about 100 μg.

Embodiment 6 is the method or composition for use of embodiment 5, wherein the dose is from about 0.1 μg to about 1 μg, about 1 μg to about 5 μg, about 5 μg to about 10 μg, about 10 μg, to about 20 μg, about 20 μg to about 50 μg, or about 50 to about 100 μg.

Embodiment 7 is the method or composition for use of any one of the preceding embodiments, wherein the method comprises intrathecal administration.

Embodiment 8 is the method or composition for use of any one of embodiments 1-6, wherein the method comprises intracisternal administration.

Embodiment 9 is the method or composition for use of any one of the preceding embodiments, wherein the RTX is administered in a pharmaceutical formulation comprising the RTX and a pharmaceutically acceptable carrier.

Embodiment 10 is the method or composition for use of embodiment 9, wherein the pharmaceutically acceptable carrier comprises water.

Embodiment 11 is the method or composition for use of embodiment 9, wherein the pharmaceutically acceptable carrier comprises saline.

Embodiment 12 is the method or composition for use of any one of embodiments 9-11, wherein the RTX is present in the pharmaceutical formulation at a concentration ranging from 1 μg/ml to 100 μg/ml.

Embodiment 13 is the method or composition for use of embodiment 12, wherein the RTX is present in the pharmaceutical formulation at a concentration ranging from 1 μg/ml to 5 μg/ml, 5 μg/ml to 10 μg/ml, 10 μg/ml to 20 μg/ml, 20 μg/ml to 50 μg/ml, or 50 μg/ml to 100 μg/ml.

Dopamine turnover is defined as the sum of concentrations of the metabolites DOPAC and HVA divided by the concentration of dopamine. **: $p<0.0001$, AAV1/2-Null Vehicle D7 versus AAV1/2-A53T Vehicle D7 (Mann-Whitney U test); : $p=0.0011$, AAV1/2-Null Vehicle D14 versus AAV1/2-A53T Vehicle D14 (Mann-Whitney U test).

Figure 6A:
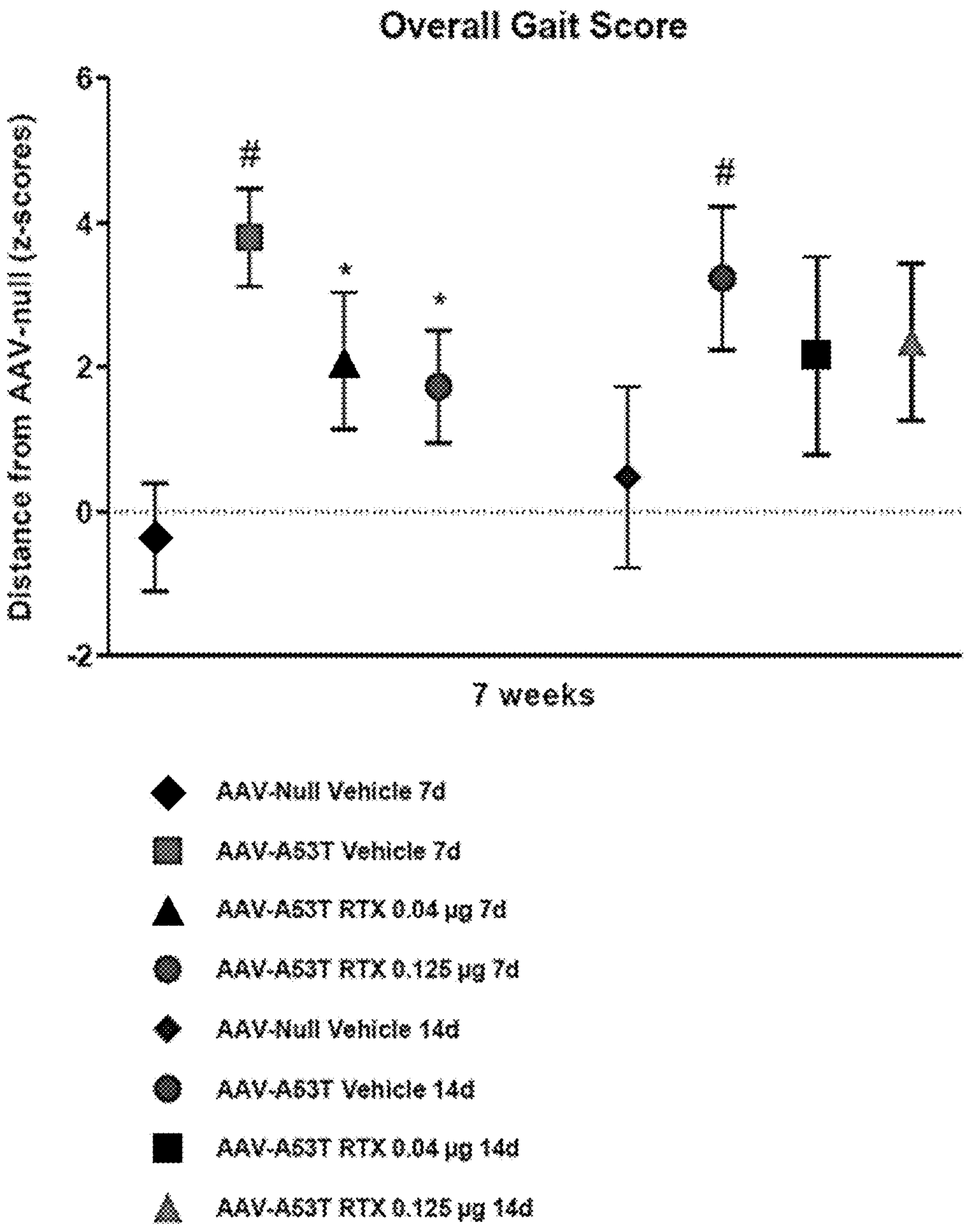
Figure 6B:
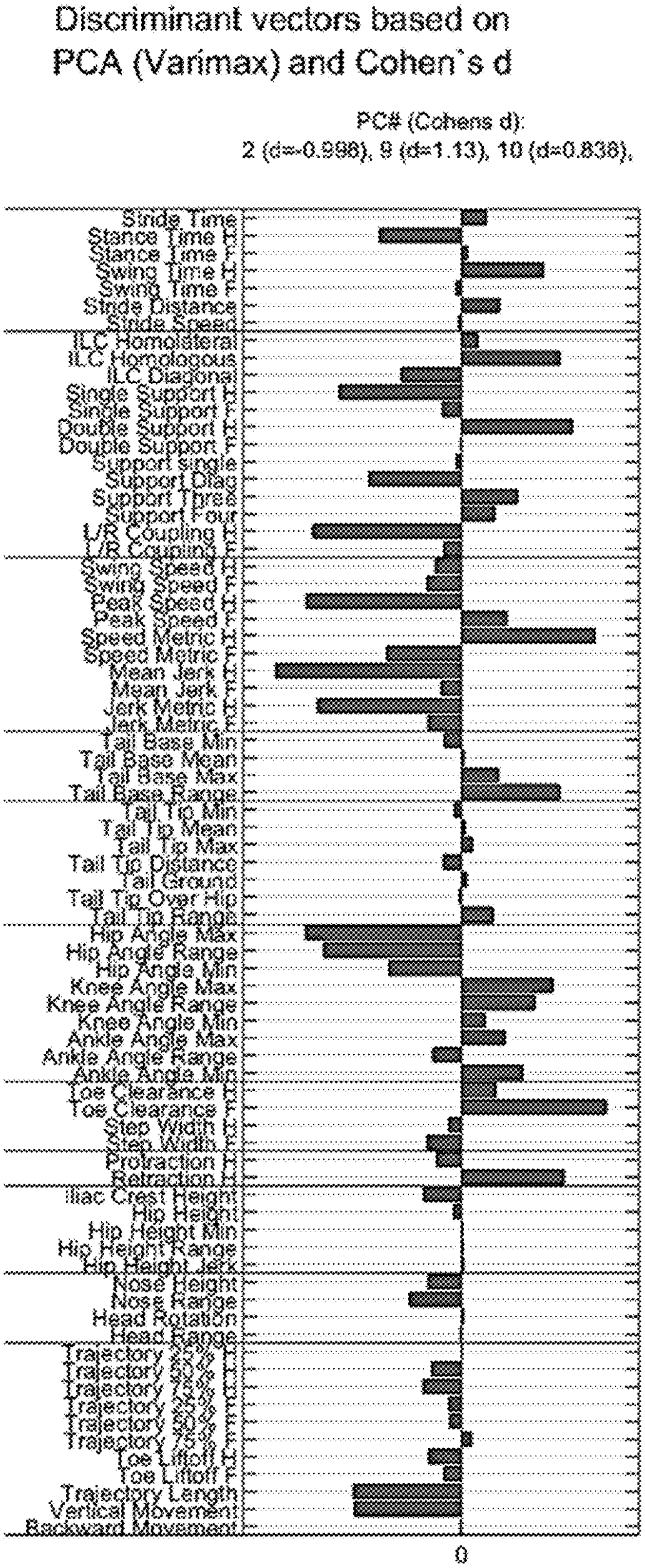

FIGS. 6A-6B show overall gait analysis scores and discriminant vectors. The Overall Gait Score of the groups dosed with RTX/vehicle at D7 and D14 after AAV1/2 delivery, shown in FIG. 6A, is based on differences in all PC scores between AAV1/2-A53T Vehicle and AAV1/2-Null Vehicle in both D7 and D14 dosing groups, using differential values of all bilaterally determined gait variables. The score can be interpreted as "how far away is an individual from the average AAV1/2-Null towards the direction of the average AAV1/2-A53T". Group means+/−95% CI are shown. The left and right halves of the graph show results for groups dosed with RTX/vehicle at D7 and D14, respectively. #: $p<0.01$, AAV1/2-A53T vehicle D7/D14 versus AAV1/2-Null vehicle D7/D14 (Unpaired t-test); *: $p<0.05$, AAV1/2-A53T vehicle D7 and AAV1/2-A53T RTX 0.04 μg D7 and AAV1/2-A53T vehicle D7 and AAV1/2-A53T RTX 0.125 μg D7 (Unpaired t-test). The discriminant vectors of the groups dosed with RTX/vehicle at D7 and D14 after AAV1/2 delivery are shown in FIG. 6B. The bar length for each individual kinematic parameter indicates how much each variable is weighted in the discriminant score (FIG. 7) and bar direction indicates the increase or decrease of parameter value in comparison to AAV1/2-Null (e.g., decrease in stride speed, or asymmetry in Hip Angle Range such that left is smaller than right).

Figure 7:
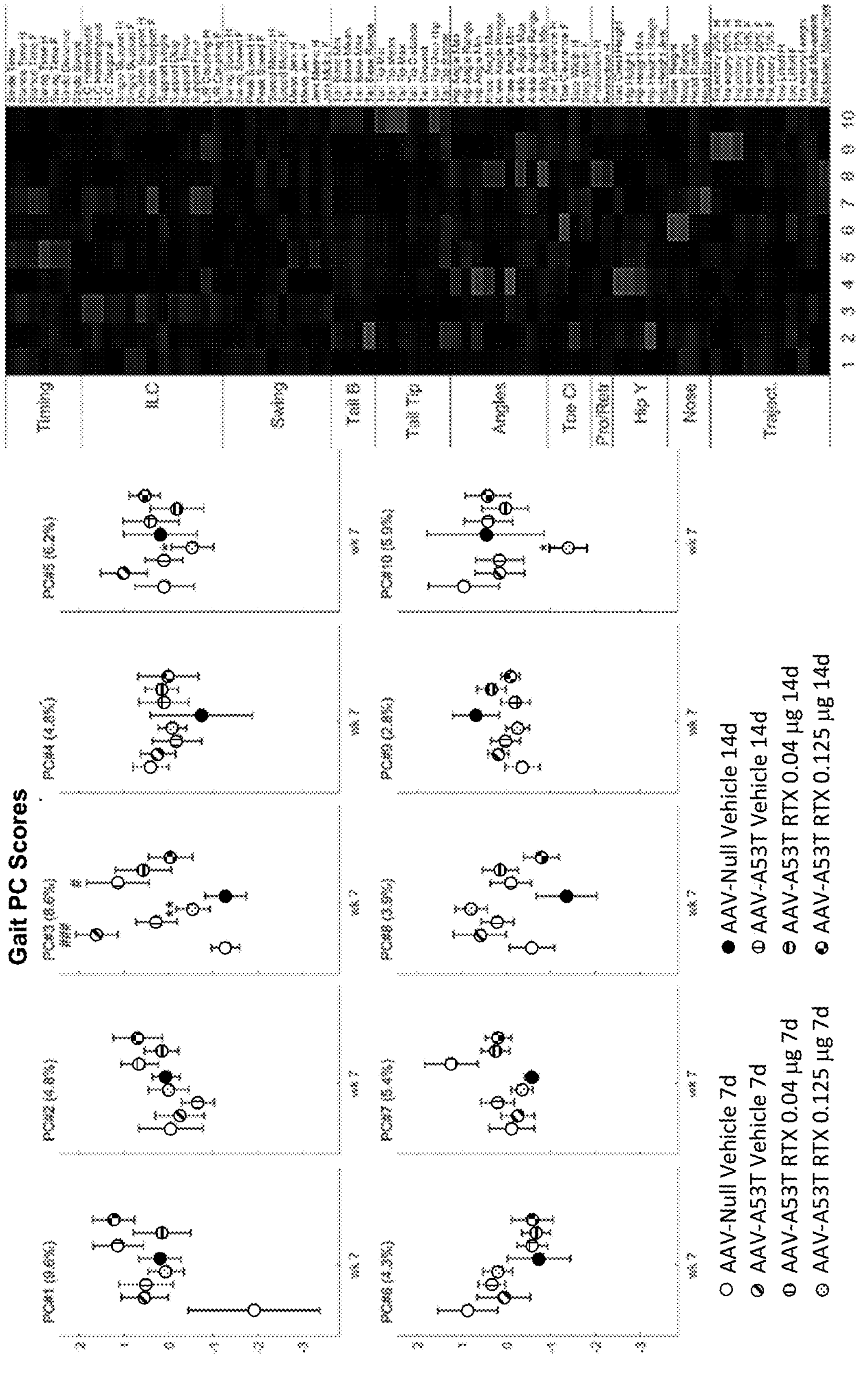

FIG. 7 shows PC scores of the gait parameters of D7 and D14 dosing groups using ten Varimax-rotated principal components. The heat map illustrates the original parameters that differentially influence each of the ten principal components. Each column of heat map shows also how the parameters correlate: red color=positive correlation, blue color=negative correlation, black=no correlation. The PC scores PC #1-PC #10 of the fine motor tests are presented at the left (group mean+/−SEM). The PC scores correspond to the PCs shown in the heat map on the right. For instance, PC #2 can be interpreted as "diagonal inter-limb coordination", including the increase in both the ILC Diagonal and Support Diagonal (diagonal, i.e., trotting cadence), and the decrease of other cadence types. The % in brackets behind the PCs on the top of each panel refer to the percentage of variation in the original data that is explained by the respective PC. #$p<0.05$, AAV-A53T Vehicle D14 versus AAV-Null Vehicle D14 (Unpaired t-test); ###$p<0.001$, AAV-A53T Vehicle D7 versus AAV-Null Vehicle D7 (Unpaired t-test); * $p<0.05$, ** $p<0.005$, AAV-A53T Vehicle D7 versus AAV-A53T RTX 0.125 μg D7. PC=principal component, ILC=interlimb coordination.

Figure 8A:
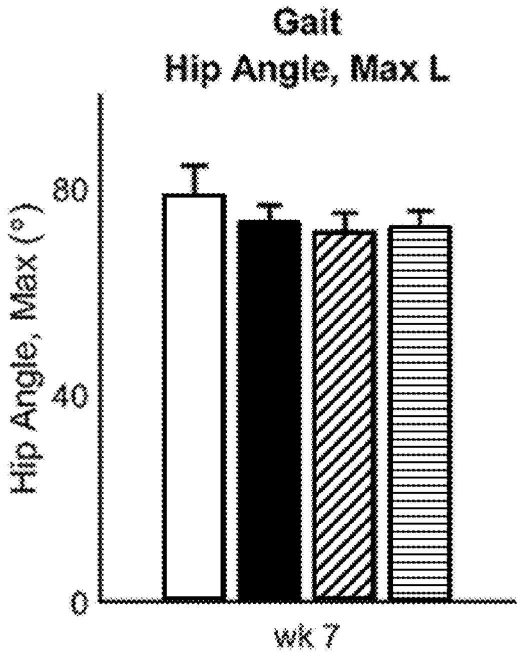
Figure 8B:
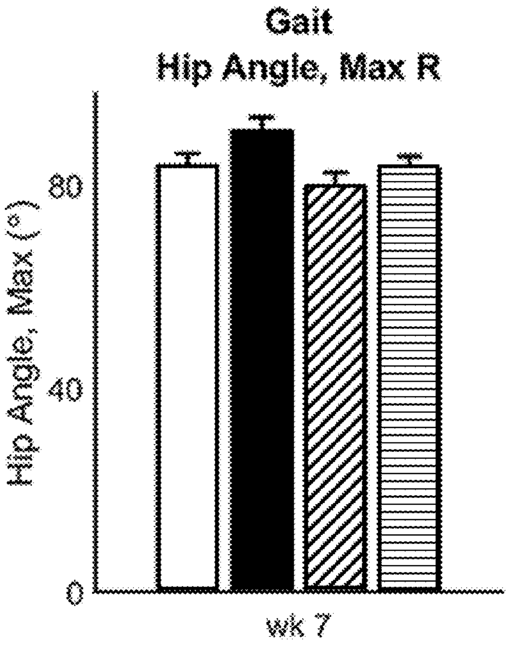
Figure 8C:
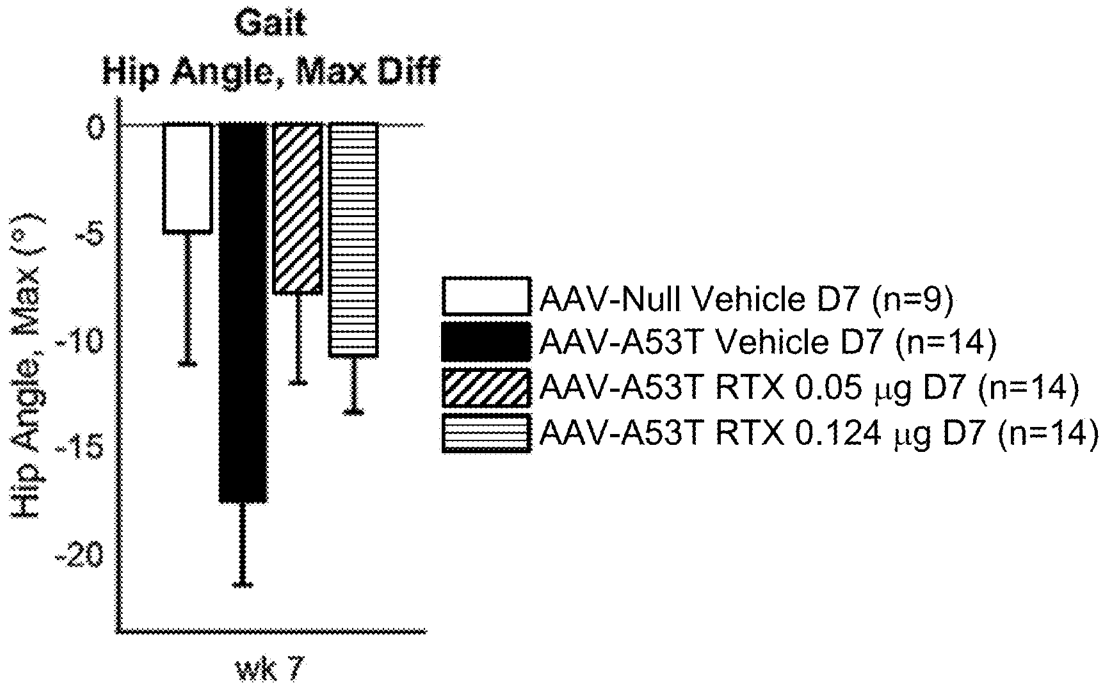

FIGS. 8A-8C show the presence of left-right asymmetry on the maximum hip angle kinematic parameter in the D7 dosing group. FIGS. 14A-14B show the left and right-side maximum hip angle respectively. The left-right difference is shown in FIG. 14C. Group means+/−SEM are shown.

Figure 9A:
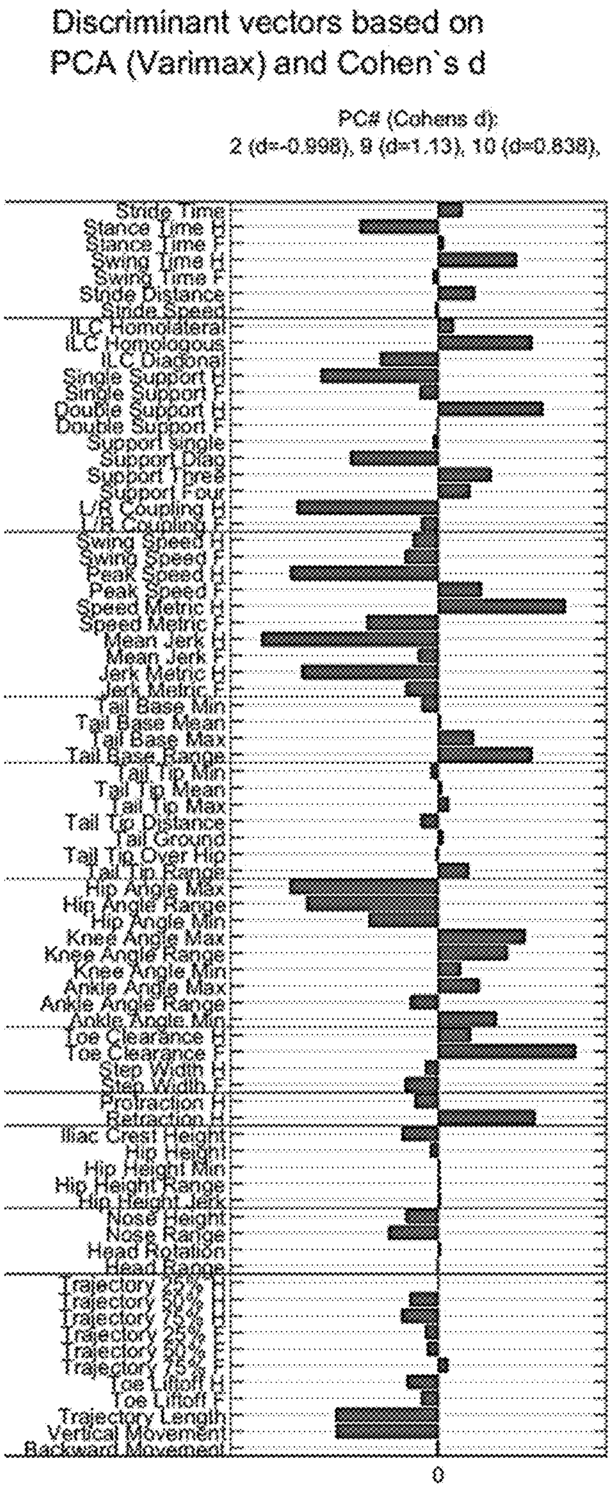
Figure 9B:
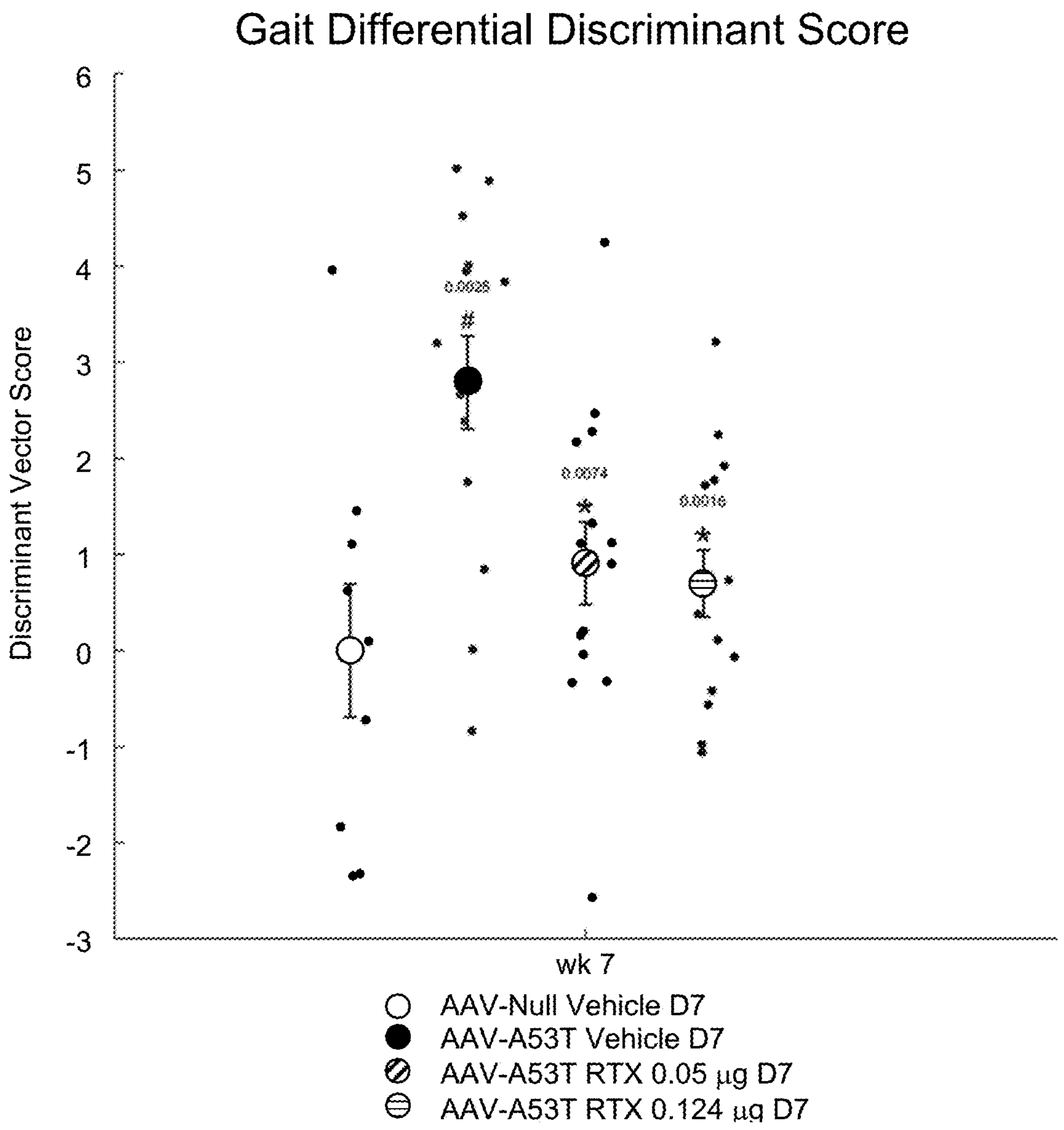

FIGS. 9A-9B show the fine motor overall gait analysis score of D7 dosing groups with emphasis to unilateral changes in left right asymmetry of gait. FIG. 9A shows discriminant vectors created using the transformed data set for 76 individual kinematic parameters, and where the left-right difference is used instead of the average of the left and right. FIG. 9B shows gait discriminant score of D7 dosing groups. The score can be interpreted as "how far away is an individual from the average AAV-Null towards the direction of the average AAV-A53T vehicle". Group means+/−SEM are shown. #: $p<0.05$ (unpaired t-test between AAV-A53T vehicle D7 and AAV-Null vehicle D7).

Figure 10A:
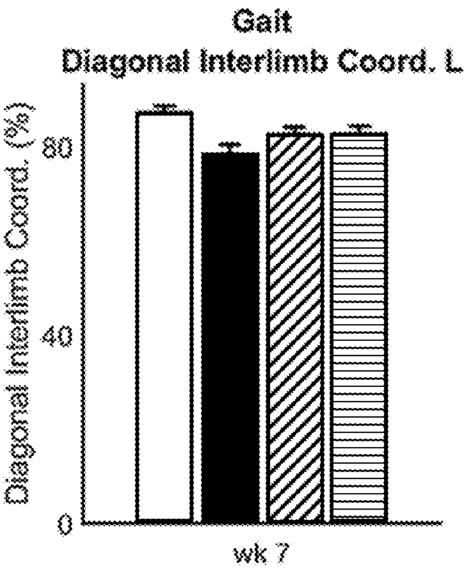
Figure 10B:
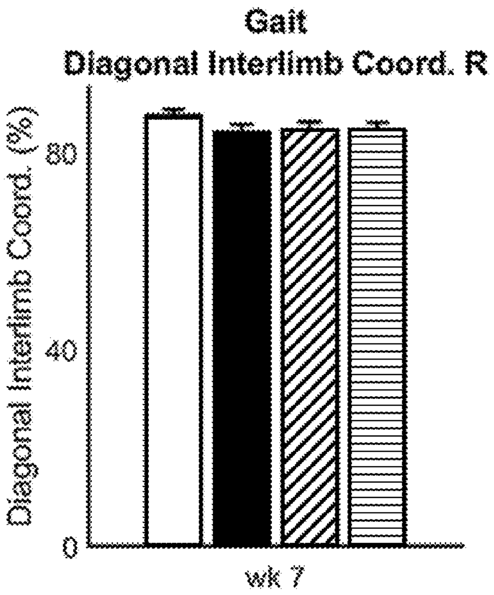
Figure 10C:
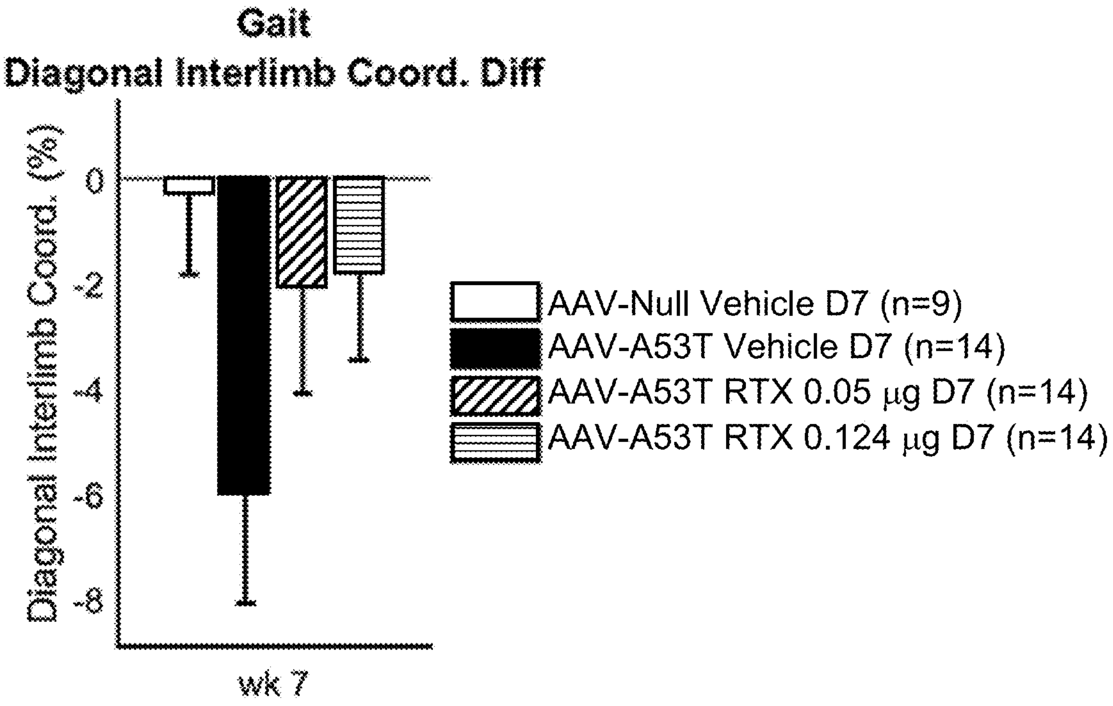
Figure 10D:
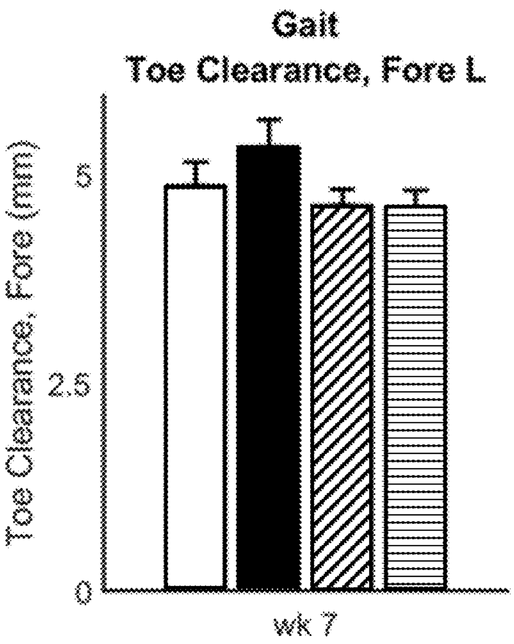
Figure 10E:
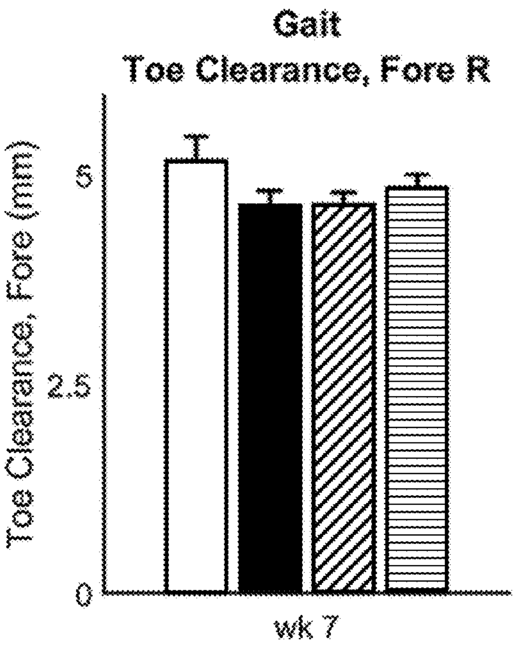

FIGS. 10A-10F show the fine motor gait analysis of the D7 dosing groups using left-right asymmetry of gait. The general gait pattern as exemplified by the diagonal interlimb coordination (or trotting) on the left side (FIG. 10A), on the right side (FIG. 10B), and the left-right difference (FIG. 10C) is shown. The body posture and balance metric, forelimb toe clearance, is shown for the left side (FIG. 10D), for the right side (FIG. 10E), and the left-right difference (FIG. 10E). Group means+/−SEM are shown.

Figure 11A:
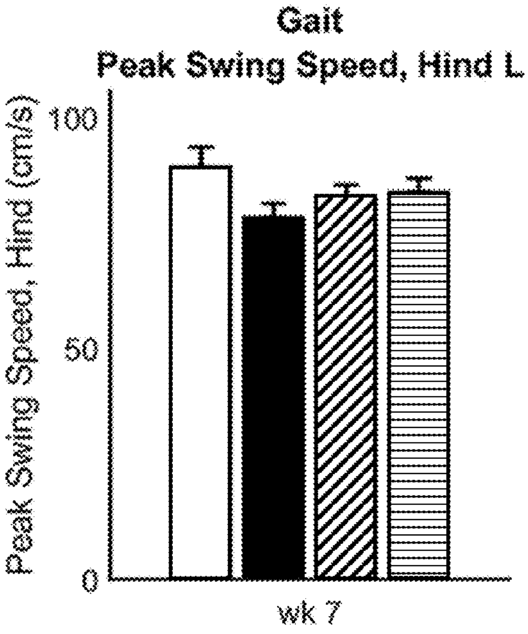
Figure 11B:
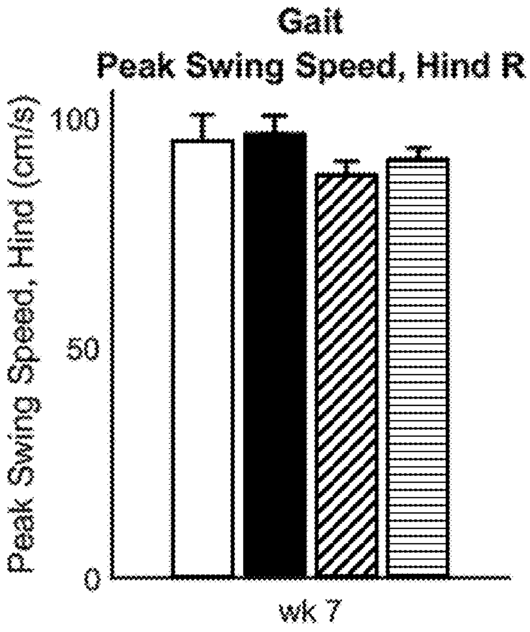
Figure 11C:
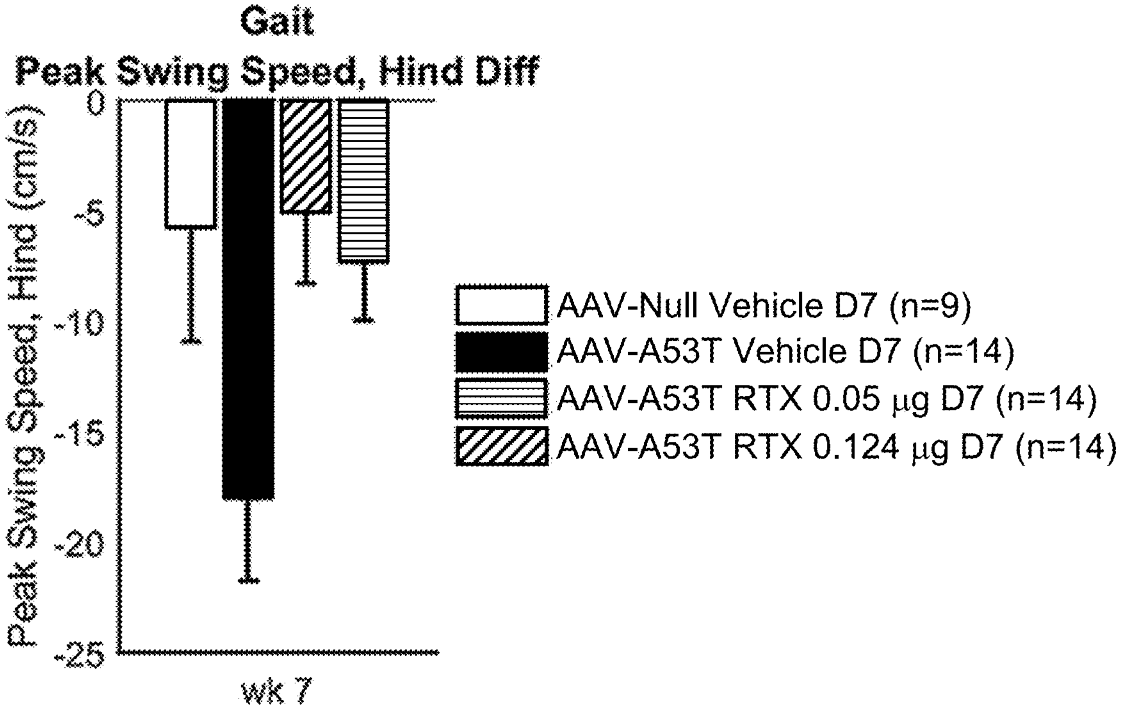
Figure 11D:
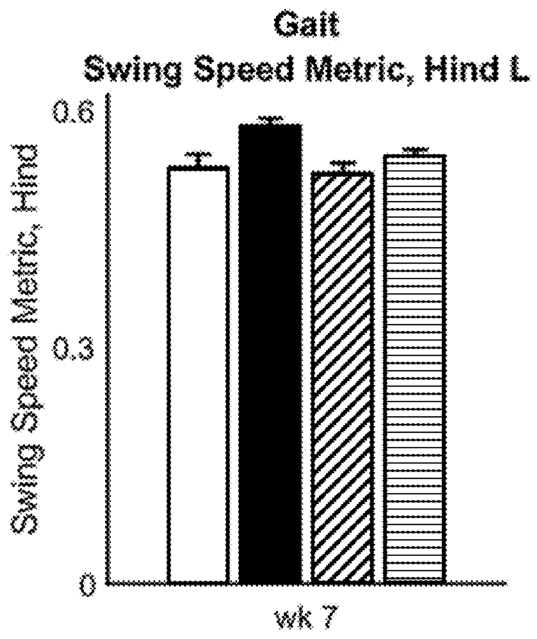
Figure 11E:
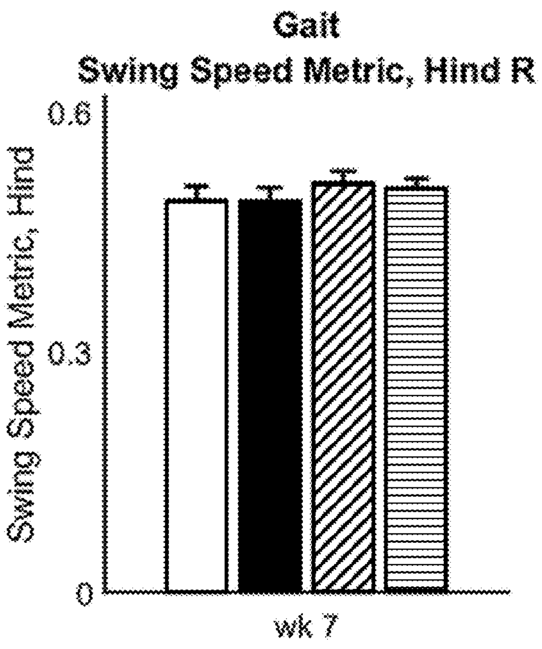
Figure 11F:
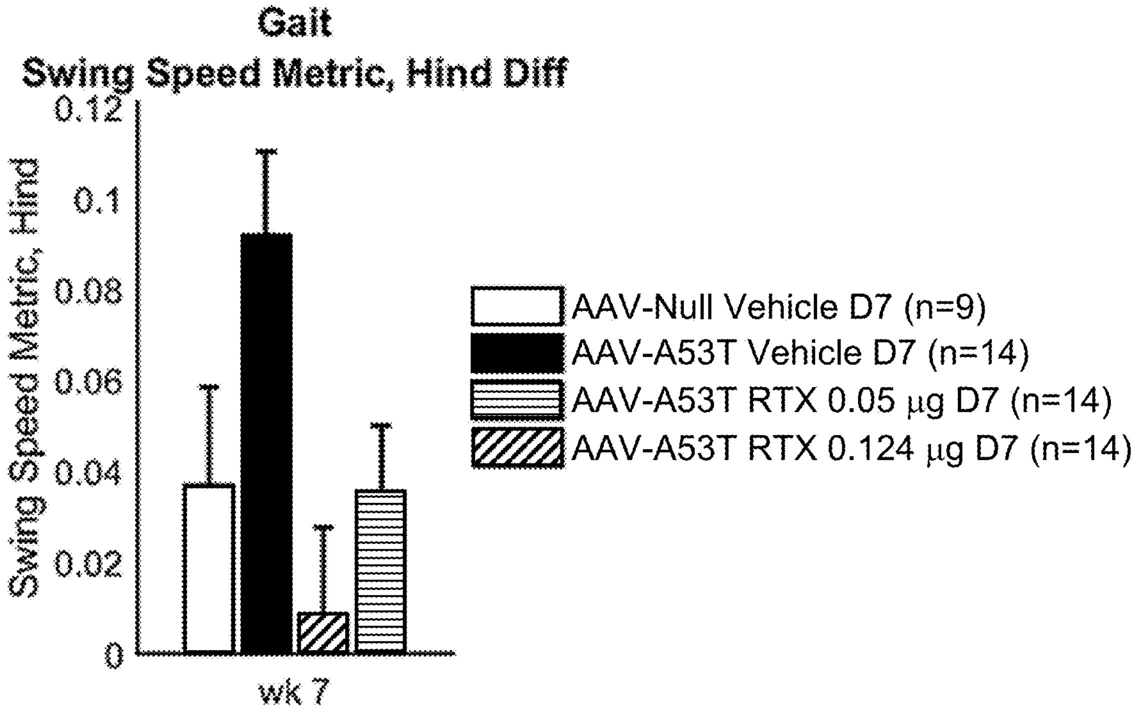

FIGS. 11A-11F show the fine motor skills analysis of the D7 dosing groups using left-right asymmetry of gait. The fine motor skills evaluated the hindlimb peak swing speed on the left side (FIG. 11A), on the right side (FIG. 11B), and the left-right difference (FIG. 11C). The hindlimb swing speed metric on the left side (FIG. 11D), on the right side (FIG. 11E), and the left-right difference (FIG. 11F). Group means+/−SEM are shown.

DETAILED DESCRIPTION

Definitions

As used herein, "intrathecally" or "intrathecal administration" refers to delivery of a drug or pharmaceutical formulation into the cerebrospinal fluid of the intrathecal space, also known as the subarachnoid space.

As used herein, "intracisternally" or "intracisternal administration" refers to delivery of a drug or pharmaceutical formulation into the cerebrospinal fluid of the brain ventricles.

"Treating" is to be understood broadly and encompasses any beneficial effect, including, e.g., delaying, slowing, or arresting the worsening of symptoms associated with PD or remedying such symptoms, at least in part. Treating also encompasses bringing about any form of improved patient function, as discussed in detail below.

"Or" is used in the inclusive sense, i.e., equivalent to "and/or," unless the context requires otherwise.

The term "about" indicates insubstantial variation in a quantity of a component of a composition not having any significant effect on the activity or stability of the composition. In some embodiments, "about" encompasses variation within 10%, 5%, 2%, 1%, or 0.5% of a stated value.

All ranges are to be interpreted as encompassing the endpoints in the absence of express exclusions such as "not including the endpoints"; thus, for example, "ranging from 1 to 10" includes the values 1 and 10 and all integer and (where appropriate) non-integer values greater than 1 and less than 10.

The terms "comprise," "comprises," "comprising," "contain," "contains," "containing," "include," "includes," and "including" are not intended to be limiting.

Exemplary Methods and Compositions for Use

Provided herein are methods of treating and compositions for use in treating Parkinson's Disease (PD) in which RTX is delivered intrathecally or intracisternally. The methods described herein are for use with any subject in whom RTX is effective, e.g., able to bind and activate TrpV1 or a homolog thereof, and who is in need of treatment for PD. In some embodiments, the RTX is administered at a dose of 0.1-100 μg. In some embodiments, the dose of RTX ranges from 0.1-0.5 μg, 0.5-1 μg, 1-2 μg, 2-5 μg, 5-10 μg, 10-20 μg, 20-30 μg, 30-40 μg, 40-50 μg, 50-60 μg, 60-70 μg, 70-80 μg, 80-90 μg, or 90-100 μg.

The concentration of RTX in the formulation may be any suitable value for delivery of the intended dose. In some embodiments, the concentration of RTX in the pharmaceutical formulation is in the range of 0.1 to 300 μg/ml. In some embodiments, the concentration of RTX in the pharmaceutical formulation is in the range of 0.1-1 μg/ml, 1-5 μg/ml, 5-10 μg/ml, 10-20 μg/ml, 10-30 μg/ml, 20-30 μg/ml, 20-50 μg/ml, 50-100 μg/ml, 100-150 μg/ml, 150-200 μg/ml, 200-250 μg/ml, or 250-300 μg/ml. In some embodiments, the concentration of RTX in the pharmaceutical formulation is in the range of 5-50 μg/ml, or 8-25 μg/ml.

Starting from a concentrated stock solution, a formulation of RTX for delivery into a subject may be prepared by dilution in an appropriate diluent, such as saline.

In some embodiments, the pharmaceutical formulation comprising the RTX and a pharmaceutically acceptable carrier has a pH in the range of 6 to 7.6. The formulation further comprises polysorbate 80 and dextrose. In some embodiments, the concentration of polysorbate 80 is 2-4% w/v, and/or the concentration of dextrose is 4-6% w/v. In some embodiments, the concentration of polysorbate 80 is 3% w/v, and/or the concentration of dextrose is 5% w/v. In some embodiments, in any of the foregoing formulations, the concentration of RTX may be 10-30 μg/ml, such as 10 μg/ml or 25 μg/ml. In some embodiments, the formulation further comprises phosphate buffer, e.g., at a concentration and pH shown for phosphate buffer in Table 1. In some embodiments, the formulation further comprises NaCl, e.g., at a concentration shown for NaCl in Table 1. When both are present, the phosphate buffer and NaCl may be (but are not necessarily) present at a combination of concentrations and phosphate buffer pH shown for an individual formulation.

TABLE 1

Exemplary RTX Solution Formulations

| Formulation Number | Formulation Components | Component Concentration |
|---|---|---|
| 1 | RTX | 200 μg/ml |
| | Polysorbate 80 | 7.0% w/v |
| | Dextrose | 0.8% w/v |
| | 30 mM Phosphate Buffer w/0.44% NaCl | 30 mM, pH 7.2 |
| 2 | RTX | 200 μg/mL |
| | Polyethylene Glycol 300 | 3.0% v/v |
| | Polysorbate 80 | 0.1% w/v |
| | Dextrose | 0.8% w/v |
| | 10 mM Phosphate Buffer w/0.73% NaCl | 10 mM, pH 6.5 |
| 3 | RTX | 200 μg/mL |
| | Polyethylene Glycol 300 | 30.0% v/v |
| | Polysorbate 80 | 1.0% w/v |
| | 10 mM Phosphate Buffer w/0.86% NaCl | 10 mM, pH 6.5 |
| 4 | RTX | 200 μg/mL |
| | Polyethylene Glycol 300 | 30.0% v/v |
| | Polysorbate 80 | 0.04% w/v |
| | 10 mM Phosphate Buffer w/0.88% NaCl | 10 mM, pH 6.5 |
| 5 | RTX | 200 μg/mL |
| | Polysorbate 80 | 3.0% w/v |
| | Dextrose | 0.8% w/v |
| | 30 mM Phosphate Buffer w/0.54% NaCl | 30 mM, pH 7.2 |
| 6 | RTX | 200 μg/mL |
| | Polysorbate 80 | 3.0% w/v |
| | Mannitol | 0.8% w/v |
| | 30 mM Phosphate Buffer w/0.54% NaCl | 30 mM, pH 7.2 |

TABLE 1-continued

Exemplary RTX Solution Formulations

| Formulation Number | Formulation Components | Component Concentration |
|---|---|---|
| 7 | RTX | 200 μg/mL |
| | Polysorbate 80 | 7.0% w/v |
| | Mannitol | 0.8% w/v |
| | 30 mM Phosphate Buffer w/0.45% NaCl | 30 mM, pH 7.2 |
| 8 | RTX | 200 μg/mL |
| | Polyethylene Glycol 300 | 3.0% v/v |
| | Polysorbate 80 | 0.1% w/v |
| | Mannitol | 0.8% w/v |
| | 10 mM Phosphate Buffer w/0.74% NaCl | 10 mM, pH 6.5 |
| 9 | RTX | 200 μg/ml |
| | Polyethylene Glycol 300 | 3.0% v/v |
| | Polysorbate 80 | 0.1% w/v |
| | Dextrose | 3.0% w/v |
| | 10 mM Phosphate Buffer w/0.34% NaCl | 10 mM, pH 6.5 |
| 10 | RTX | 200 μg/mL |
| | Polyethylene Glycol 300 | 3.0% v/v |
| | Polysorbate 80 | 0.1% w/v |
| | Mannitol | 3.0% w/v |
| | 10 mM Phosphate Buffer w/0.36% NaCl | 10 mM, pH 6.5 |
| 11 | RTX | 200 μg/ml |
| | Polysorbate 80 | 0.03% w/v |
| | Dextrose | 0.05% w/v |
| | 30 mM Phosphate Buffer w/0.54% NaCl | 30 mM, pH 7.2 |

RTX for treating PD can be administered intrathecally or intracisternally. For intrathecal administration, when the PD treatment emphasis is on motor coordination in the hands (hand motor coordination is a frequent issue for PD patients) the intrathecal administration should be focused on the cervical or thoracic region of the spinal column. Intracisternal administration is preferred for a whole body approach for PD treatment. Alternatively, RTX can be administered intrathecally to the top of the spinal column at C1-C5.

Significantly, a method within the scope of the present disclosure can provide improved patient function. "Improved patient function" can be defined as an improvement measured by any one or more factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

Example 1. Effects of Single Intrathecal Administration of RTX on the AAV-A53T Mouse Model of Parkinson's Disease-Like (PD) Pathology Using an in vivo mouse study for a Parkinson's Disease (PD), the disease state was first induced in C57Bl/6J male mice at 8 weeks of age by unilateral adenovirus vector (AAV) infusion to substantia nigra (SN) in the right hemisphere of the brain. The vector contained a construct configured to overexpress mutated human A53T-α-synuclein, which leads to the degeneration of nigral dopaminergic neurons and reduction of dopamine levels in the striatum. This has been shown to lead to PD-like symptoms including motor deficits.

In total, 142 C57Bl/6J mice (126 males and 16 females) aged 2 months of age at the start of the study were housed at a standard temperature (22±1° C.) and in a light-controlled environment (lights on from 7 am to 8 pm) with ad libitum access to food and water.

The purpose of this study was to investigate the effects of single intrathecal administration of RTX on the AAV-A53T mouse model of PD-like pathology. Prior to this study start, a pilot tolerability study was conducted in which 16 male and 16 female C57Bl/6J mice were infused with RTX at two doses (either 0.04 μg or 0.125 μg) and followed up for 24 hours thereafter to observe any possible adverse effects of the treatment.

Of the 32 total mice used in the pilot study arm, in total 4 mice died during the 24 hour monitoring period after intrathecal infusion of RTX. Two females treated with 0.125 μg dose were found dead in cage within 4-24 hours after infusion due to unknown reason. In addition, one female and one male mouse from the same dosing group died immediately after infusion of RTX. No significant adverse effects were observed in the rest of the mice.

For this study, a total of 110 male C57Bl/6J mice two months of age were infused with either AAV-A53T (90 mice) or AAV-Null (20 mice) into substantia nigra unilaterally to induce PD-like pathology or to serve as sham controls, respectively. Mice infused with AAV-Null (empty) vector ("sham-infused" mice) were used in order to control for the effect of the viral infusion. After 7 or 14 days of AAV-A53T mediated disease model induction, the mice were treated with RTX (0.04 μg or 0.125 μg) (5 μL volume, prepared from a 25 μg/ml RTX solution containing Polysorbate 80 at 0.03% w/v, dextrose at 0.05% w/v, Phosphate Buffer at 30 mM, and NaCl 0.54% w/v, pH 7.2, and diluted in saline as needed) by single intrathecal infusion at lumbar spinal cord area. One AAV-Null and AAV-A53T infused group per each time point were treated with vehicle instead of RTX.

The mice were then treated with RTX or vehicle by intrathecal infusion 7 or 14 days after AAV infusion. The mice were assigned to treatment groups as follows:

- Group 1: 10 male mice sham-infused with AAV-null, and administered vehicle at D7.
- Group 2: 15 male mice infused with AAV-A53T, and administered vehicle at D7.
- Group 3: 15 male mice infused with AAV-A53T, and administered 0.04 μg of RTX at D7.
- Group 4: 15 male mice infused with AAV-A53T, and administered 0.125 μg of RTX at D7.
- Group 5: 10 male mice sham-infused with AAV-null, and administered vehicle at D14.
- Group 6: 15 male mice infused with AAV-A53T, and administered vehicle at D14.
- Group 7: 15 male mice infused with AAV-A53T, and administered 0.04 μg of RTX at D14.
- Group 8: 15 male mice infused with AAV-A53T, and administered 0.125 μg of RTX at D14.

Body weight of the animals was monitored two times per week. Fine motor kinematic analysis was performed 7 weeks after AAV infusion. 8 weeks post AAV infusion, the mice were euthanized and subjected to tissue sample collection. Dopamine and its metabolites were analyzed from ipsilateral and contralateral *striata* by high performance liquid chromatography (HPLC).

All surgical procedures were performed under aseptic conditions and sterile materials, solutions and equipment were used when applicable. Handling of viral material and stereotactic infusions were performed in biosafety level 2 (BSL-2) laminar hood (BioWizard Golden line 130, Kojair) and study related behavioral tests were performed in BSL-1 status facilities. Surgical procedures and housing of the mice up to 1 week after AAV-vector infusion were performed according to BSL-2 level safety regulations (Council Directive 90/679/EEC) and facilities.

First, the mice were anesthetized with 5% isoflurane (in 70% $N_2O$ and 30% $O_2$; flow 300 ml/min) and placed in a stereotactic frame. During the operation the concentration of anesthetic was reduced to 1-1.5%. The rectal temperature was maintained at 37.0±1.0° C. with a homeothermic blanket system. The skin was opened by a medial incision and retracted laterally. The right brain hemisphere was exposed through a small craniectomy to the skull. The dura mater was carefully removed with fine forceps and a stereotaxic injection with either AAV-Null Empty (5.1×1012 vg/mL), or AAV-A53T (5.1×1012 vg/mL) was performed as follows: A blunt injection needle (30 G) connected to a 10 μL Hamilton microsyringe mounted on a digitally guided infusion unit (Digital Lab Standard™, Harvard Apparatus) and pump (Pump 11, Elite Nanomite, Harvard Apparatus) was lowered into the level of substantia nigra. AAV material was infused unilaterally to the substantia nigra at following coordinates (relative to the bregma): AP=3.0 mm posterior; ML=1.3 mm; DV=4.2 mm to the skull surface. A total of 2 μL of the vector was be infused at a speed of 0.4 μL/min. After infusion, the cannula was left in place for another 5 min before being withdrawn. The skin was thereafter closed and disinfected. The mice were then allowed to recover from anesthesia and were carefully monitored for possible post-surgical complications. After initial recovery, the animals were returned to the home cages with ad libitum access to food and water.

Mice were administered RTX or vehicle intrathecally 7 or 14 days after AAV-A53T or AAV-Null infusion. First, the mice were anaesthetized using 2-5% isoflurane and set on prone position on the surgery platform. After shaving the target area of the skin, Xylocain gel (2% Lidocain) was introduced to the area. 5 minutes later, gel was removed, and scrubbing by iodine solution was done as antiseptic preparation for skin incision.

The laminectomy was performed lumbar (L5) level exposing the cord without disrupting the dura mater. A cannula attached to a 10 μL Hamilton syringe mounted on a microinfusion system (Harvard Apparatus) was inserted into the subarachnoid space and advanced to the level of L5-L6, by carefully lowering up to 10 to 15 mm under dura membrane so that opening of the needle was in the desired location. Junction between needle and dura opening was sealed with tissue sealant adhesive (Tisseel® Duo Quick, Baxter) and infusion was started. 5 μL of formulated resiniferatoxin was injected at the rate of 0.5 μL/min after which the cannula was withdrawn from the intrathecal space after a 5 min stabilization period. Immediately following withdrawal, another thin layer of tissue sealant adhesive was applied to close the opening in the dura to avoid leakage. Thereafter muscles and the skin were closed in layers and disinfected. The mice were allowed to recover in homeothermic cages before returning them to home cage.

Before AAV and intrathecal infusion surgery, the mice were given buprenorphine (Temgesic®, 0.06 mg/kg, 2 mL/kg). Additional doses of buprenorphine were administered twice-a-day during the following 48 h resulting in altogether five administrations. All mice were also monitored for dehydration and given 0.9% sterile saline (i.p.) following surgery and additionally as needed.

Body weight of the mice was measured twice-per week (on Mondays and Fridays) for the whole study duration.

8 Weeks after AAV-A53T infusion, the mice were terminally anesthetized with intraperitoneal injection of pentobarbital (Mebunat®, Orion Pharma). About 500 μL of blood was then collected by terminal cardiac puncture and transferred to pre-chilled $K_2$-EDTA tubes. Plasma was separated immediately thereafter by centrifugation (2000 g, 10 min+4° C.). Thereafter, 150 μL of plasma was collected in 2.0 mL polypropylene tubes and frozen on dry ice. The plasma samples were stored at −80° C. until shipped to Sorrento Therapeutics, Inc. on dry ice. After blood collection, the mice were transcardially perfused with heparinized (2.5 IU/mL) saline in order to remove blood from the brain. Immediately after perfusion, the brains were dissected on ice.

Ipsi- and contralateral striatum were collected in 1.5 mL Eppendorf tubes, snap-frozen on dry ice (i.e. left and right separately), weighed and stored at −80° C. for HPLC analysis of dopamine and its metabolites.

Dopamine (DA), 3,4-dihydroxyphenylacetic acid (DOPAC) and homovanillic acid (HVA) concentrations in mouse striatal tissue samples were determined by high performance liquid chromatography (HPLC) method with electrochemical detection. After thawing on ice, tissue samples were homogenized (1:10, w/v) in 0.1 M perchloric acid with MSE Soniprep 150 ultrasonic disintegrator (MSE Scientific Instruments, Crawley, UK). Tissue homogenates were centrifuged for 15 min at 15000 g at 4° C. Supernatants were filtered through polypropylene membrane (GHP Acrodisc 13 0.45 μm, Pall Corporation, Ann Arbor, MI, USA) and diluted (1:1) with 0.1 M perchloric acid. The samples were transferred into plastic vials and analyzed immediately.

The ESA HPLC system (ESA Inc., Chelmsford, MA, USA) consists of a 582 solvent delivery system, a DG-1210 vacuum degasser, an 542 autosampler, a 880 thermostatted chamber, an eight-channel CoulArray® 5600 electrochemical array detector equipped with a two-channel 5014B microdialysis cell and a CoulArray® for Windows data acquisition module (version 1.00). The applied potentials are −175 mV (channel 1), +225 mV (channel 2), +350 mV (channel 3) and +450 mV (channel 4). DA and DOPAC are detected on channel 2 and HVA on channel 3. Injection volume is 10 μl.

The analytes were separated on a Zorbax SB-Aq reversed-phase column (2.1×100 mm, 3.5 μm, Agilent Technologies Inc., Little Falls, Wilmington, DE, USA) with a Zorbax SB-Aq precolumn (2.1×12.5 mm, 5 μm) in an isocratic run. The column was maintained at 35° C. The mobile phase was 100 mM monobasic sodium phosphate containing 4.75 mM citric acid monohydrate, 7 mM 1-octanesulfonic acid and 50 μM disodium EDTA-acetonitrile mixture (98:2, v/v). The pH of the mobile phase was adjusted to 2.2 with o-phosphoric acid. The flow rate was 0.3 mL/min. The levels of DA, DOPAC and HVA were expressed as nmol/g wet tissue.

The fine motor skills of the mice were evaluated 7 weeks post infusion (MotoRater, TSE Systems, Homburg, Germany) using walking mode. On the day of testing the mice were marked in appropriate points of body, such as joints of limbs and parts of tail to ease the data analysis process. The movement data was captured using a high-speed camera (300 frames/second) from three different dimensions, from below and both sides. Different gait patterns and movements were analyzed using a custom-made automated analysis system. The analyzed parameters include: 1) general gait pattern parameters (stride time and speed, step width, stance and swing time during a stride, interlimb coordination), 2) body posture and balance (toe clearance, iliac crest and hip height, hind limb protraction and retraction, tail position and movement), and 3) fine motor skills (swing speed during a stride, jerk metric during swing phase, angle ranges and deviations of different joints, vertical and horizontal head movement).

The gait parameters always have several (and complex) inter-correlations. For example, a shorter stride duration and longer step lengths lead to higher speed. Different "gait features", which are manifested in sets of highly correlating parameters, can be identified using Principal Component Analysis (PCA). Principal Component Analysis is a statistical tool to compact the information in a multivariate data set, reveal correlations between original variables, and ultimately, create a small set of new and sensitive uncorrelated parameters, the principal components (PC).

PCA is a linear transformation based on principal component coefficients and eigenvectors. The transformed, new, uncorrelated variables are called the PC scores. The first principal component (PC) corresponds to such linear combination of data which has the largest possible variance. The second PC has again the largest possible variance of what is left when the proportion of the first PC is discarded, and so on for the rest of the PCs. The eigen vectors also reveal information about the internal structure of the data, i.e., mutually correlated parameters. Each PC score represent combined information of all the parameters which are emphasized in the corresponding PC. The number of PCs used was determined using Kaiser criterion (eigenvalue>1.0).

PC results interpretation was simplified using eigenvector rotation technique. Rotation is a procedure in which the eigenvectors are manipulated to achieve simple structure, or the number of clearly non-zero elements of each eigenvector is optimized to be as low as reasonably possible. In this study, we used the orthogonality preserving, Varimax rotation procedure.

Finally, an overall gait analysis score based on PCA was determined. The score is based on differences between the AAV-null vehicle and the AAV-A53T vehicle groups in all the PC scores (Gait Overall Score), or in those PCs which demonstrate large effect size (Gait Discriminant Score). Thus, the purpose of that score is to identify a disease model specific combination of original variables—a "fingerprint"—which characterizes the disease model in the best possible way and differentiates the two groups. After the "fingerprint", or discriminant direction vector, has been determined, the overall gait analysis scores can be obtained by projecting the (normalized) parameter data of each individual mouse onto the discriminant direction vector. Ultimately, the overall kinematic effects of a pharmacological agent can be seen in a highly sensitive manner.

Animals were monitored daily by laboratory personnel. In the case that general health status of an animal had significantly worsened, it was sacrificed by an overdose of $CO_2$, and decapitated. Definitions of acceptable endpoints included: no spontaneous movements and inability to drink or eat in a 24-h observation period, massive bleeding, spontaneous inflammation, missing anatomy, swelling or tumors larger than 20 mm, and inability to right itself for a 30-s period.

During the study, one mouse was lost from groups 1, 2, 3, 4, 5 and 8. Mice from groups 3, 4 and 8 died during or right after infusion under anesthesia. Mice from groups 1, 2 and 5 were euthanized one day after intrathecal administration due to meeting an end-point criterion.

Figure 1:
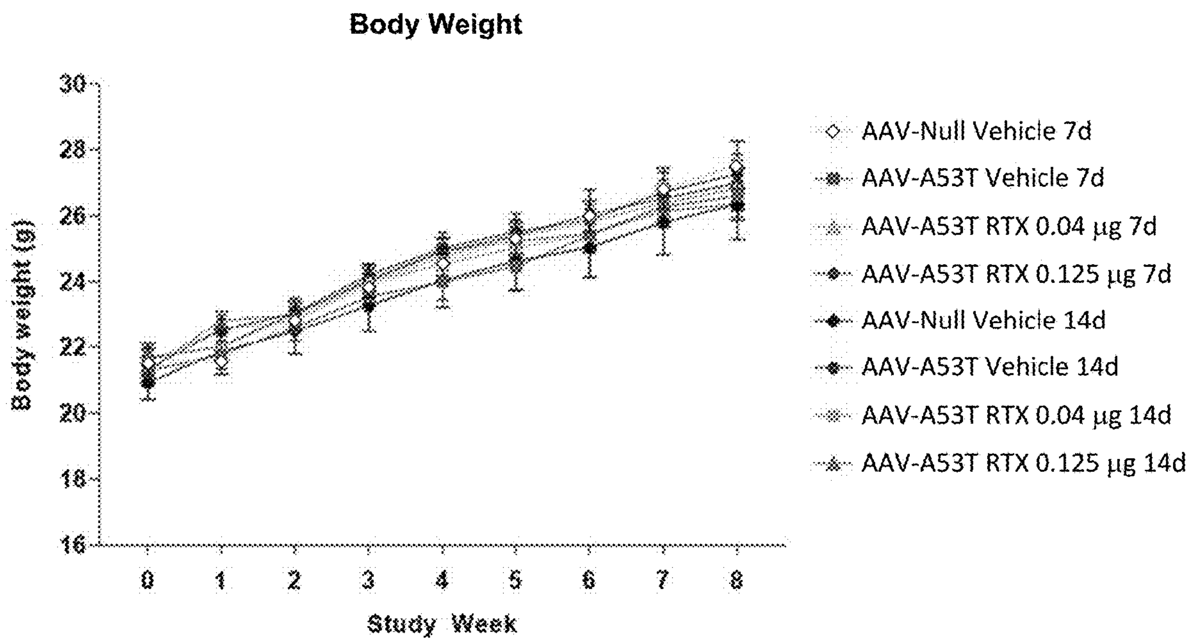
FIG. 1 shows effects of a single administration of resiniferatoxin (RTX) at a low dose of 0.04 μg or at a high dose of 0.125 μg, 7 or 14 days after AAV-A53T or AAV-Null infusion on the body weight (g) of C57Bl/6J male mice. No significant differences between the groups were observed (two-way ANOVA) during the eight week study period.

The effects of a single administration of 0.04 μg or 0.125 μg RTX 7 or 14 days after AAV-A53T or AAV-Null infusion on the body weight of C57Bl/6J male mice are presented in FIG. 1. No significant differences between the groups were observed (two-way ANOVA) during the 8 week study duration.

The effects of single administration of resiniferatoxin at two doses 7 or 14 days after unilateral AAV-A53T or AAV-Null infusion on the dopamine and its metabolite levels in the ipsilateral and contralateral striatum of C57Bl/6J male mice are presented in FIGS. 2-5. The analysis was performed with HPLC. For statistical analysis, AAV-Null infused groups were first compared to AAV-A53T groups treated intrathecally with vehicle to observe the effect of A53T $\alpha$-synuclein transgene insertion only. Thereafter, the AAV-A53T vehicle group was compared to AAV-A53T groups treated with 0.04 μg or 0.125 μg of resiniferatoxin to observe possible treatment effects of resiniferatoxin. Day 7 and Day 14 groups were analyzed separately.

Figure 2:
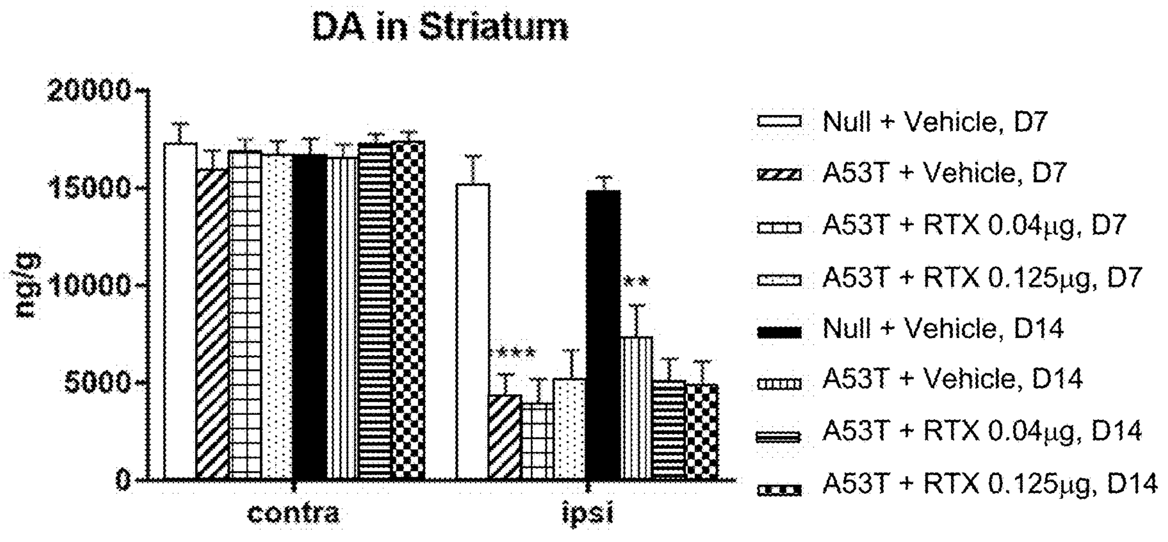
FIG. 2 shows effects of single administration of resiniferatoxin at a low dose of 0.04 μg or at a high dose of 0.125 μg, 7 or 14 days after unilateral AAV-A53T or AAV-Null infusion on the dopamine levels (ng/g) in the ipsilateral and contralateral striatum of C57Bl/6J male mice. AAV-A53T infusion resulted in significant reduction in dopamine levels in ipsilateral striatum at both time points treated intrathecally with vehicle. *: $p<0.0001$, AAV1/2-Null Vehicle D7 versus AAV1/2-A53T Vehicle (Unpaired t-test); : $p=0.016$, AAV1/2-Null Vehicle D14 versus AAV1/2-A53T Vehicle D14 (Unpaired t-test).

The effects of single administration of RTX at two doses 7 or 14 days after unilateral AAV-A53T or AAV-Null infusion on the dopamine (DA) levels in the ipsilateral and contralateral striatum of C57Bl/6J male mice are presented in FIG. 2. AAV-A53T infusion resulted in significant reduction in dopamine levels in ipsilateral striatum at both time points treated intrathecally with vehicle. There was a minor trend towards higher dopamine levels in the mice treated with high dose of resiniferatoxin 7 days after AAV-A53T infusion. This difference was however statistically non-significant (one-way ANOVA). On the contrary, a minor opposite and non-significant trend of lower dopamine levels was observed in groups treated with resiniferatoxin at day 14.

Figure 3:
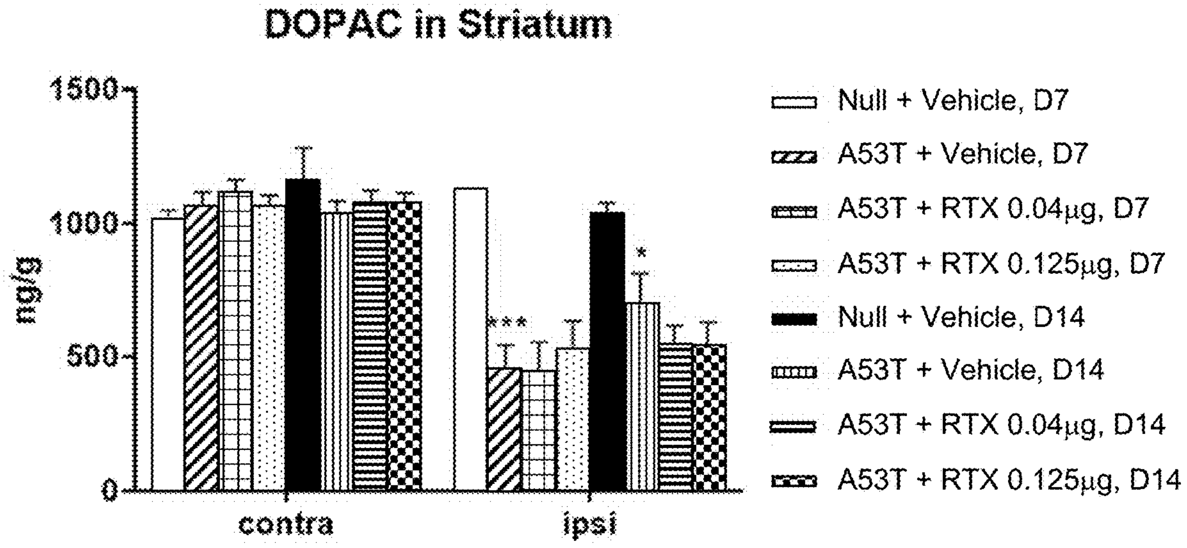
FIG. 3 shows the effects of single administration of resiniferatoxin at low and high doses 7 or 14 days after unilateral AAV-A53T or AAV-Null infusion on the levels (ng/g) of 3,4-Dihydroxyphenylacetic acid (DOPAC) in the ipsilateral and contralateral striatum of C57Bl/6J male mice. ***: $p=0.003$, AAV1/2-Null Vehicle D7 versus AAV1/2-A53T Vehicle (Unpaired t-test); *: $p<0.05$, AAV-Null+Vehicle D14 versus AAV-A53T+Vehicle D14 (unpaired t-test).

The effects of single administration of RTX at two doses 7 or 14 days after unilateral AAV-A53T or AAV-Null infusion on the levels of 3,4-Dihydroxyphenylacetic acid (DOPAC) in the ipsilateral and contralateral striatum of C57Bl/6J male mice are presented in FIG. 3. AAV-A53T infusion resulted in significant reduction in DOPAC levels in ipsilateral striatum at both time points treated intrathecally with vehicle. There was a minor trend towards higher DOPAC levels in the mice treated with high dose of resiniferatoxin 7 days after AAV-A53T infusion. This difference was however statistically non-significant (one-way ANOVA). A minor opposite and non-significant trend of lower DOPAC levels was observed in groups treated with resiniferatoxin at day 14.

Figure 4:
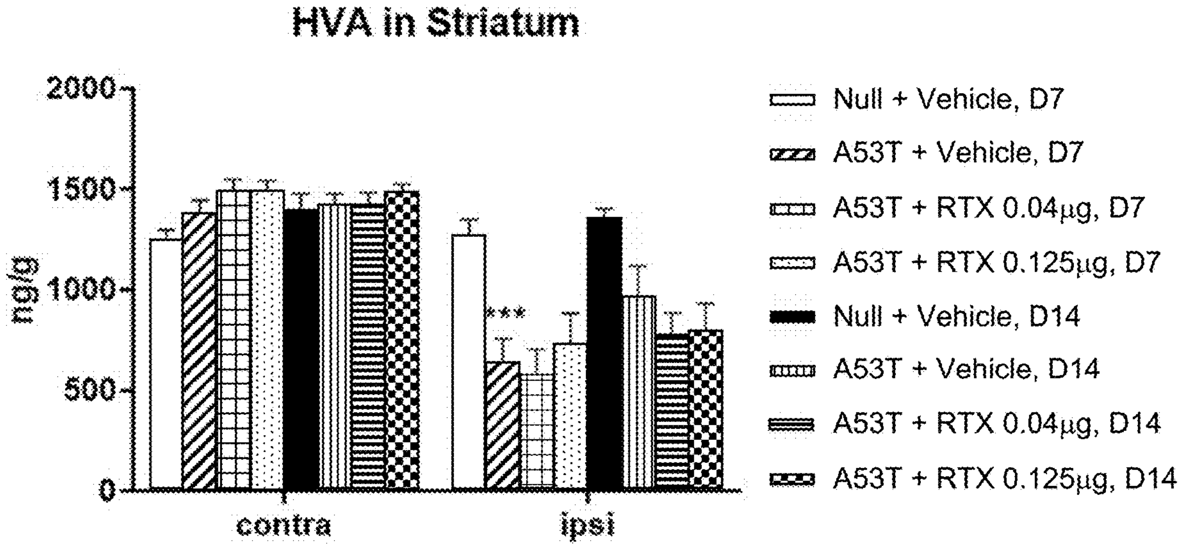
FIG. 4 shows effects of single administration of resiniferatoxin at low and high doses 7 or 14 days after unilateral AAV-A53T or AAV-Null infusion on the levels (ng/g) of homovanillic acid (HVA) in the ipsilateral and contralateral striatum of C57Bl/6J male mice. ***: $p=0.0007$, AAV1/2-Null Vehicle D7 versus AAV1/2-A53T Vehicle (Unpaired t-test) (Unpaired t-test).

The effects of single administration of RTX at two doses 7 or 14 days after unilateral AAV-A53T or AAV-Null infusion on the levels homovanillic acid (HVA) in the ipsilateral and contralateral striatum of C57Bl/6J male mice are presented in FIG. 4. AAV-A53T infusion resulted in significant reduction in HVA level in ipsilateral striatum at both time points treated intrathecally with vehicle. There was a minor trend towards higher concentration in the mice treated with high dose of resiniferatoxin 7 days after AAV-A53T infusion. This difference was however statistically non-significant (one-way ANOVA). A minor opposite and non-significant trend of lower HVA levels was observed in groups treated with resiniferatoxin at day 14.

Figure 5:
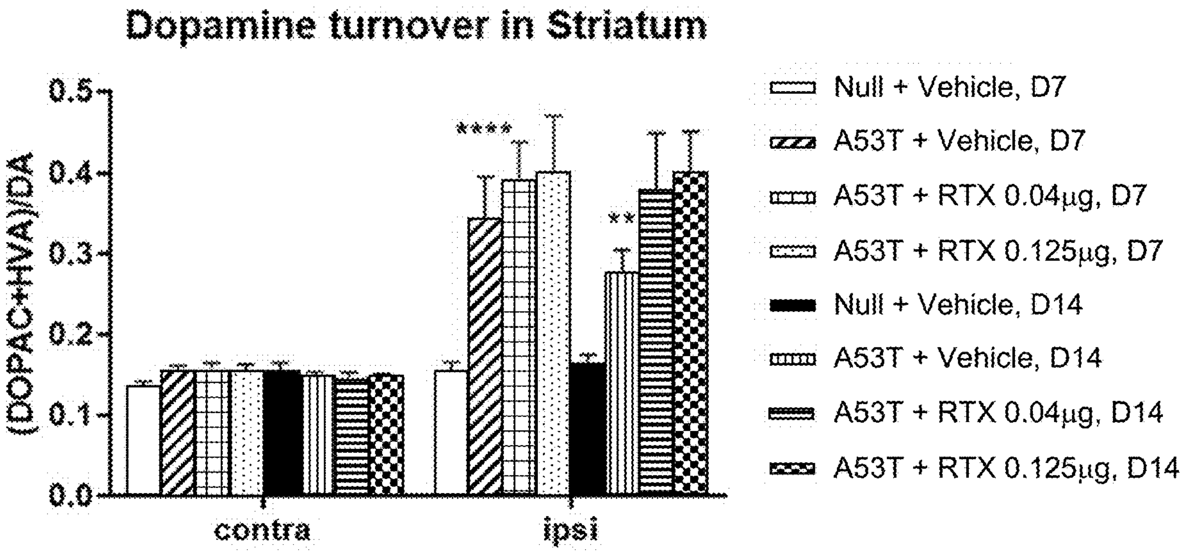
FIG. 5 shows effects of single administration of resiniferatoxin at low and high doses 7 or 14 days after unilateral AAV-A53T or AAV-Null infusion on dopamine turnover in ipsilateral and contralateral striatum of C57Bl/6J male mice.

The effects of single administration of RTX at two doses 7 or 14 days after unilateral AAV-A53T or AAV-Null infusion on dopamine turnover in ipsilateral and contralateral striatum of C57Bl/6J male mice are shown in FIG. 5. Dopamine turnover is defined as the sum of concentrations of the metabolites DOPAC and HVA divided by the concentration of dopamine. AAV-A53T infusion resulted in significantly increased turnover of dopamine in ipsilateral striatum at both time points treated intrathecally with vehicle. There was a minor trend towards even higher turnover rates in the mice treated with both doses of resiniferatoxin 7 and 14 days after AAV-A53T infusion. These treatment effects were however statistically non-significant (Kruskal-Wallis test).

To examine whether unilateral AAV1/2-A53T-aSyn injection resulted in motor impairment the fine motor skills and gait deficits were measured using kinematic gait analysis at 7 weeks after the AAV1/2 infusion.

First, 95 gait parameters of each analyzed gait cycle were assessed. Parameter values of left and right sides were initially determined separately if possible. Most distinct AAV1/2-A53T-induced gait differences with respect to AAV1/2-Null control group ($p<0.05$, Unpaired t-test, assumption of unequal variances) were related to interlimb coordination and overall decrease of speed: Hind limb (D7 and D14) and fore limb (D14) stance times were increased, homolateral gait (pace) was increased (D7 and D14), diagonal gait (trot) decreased (both D7 and D14, seen in the support diagonal parameter), double support and duty cycle, especially in hind limbs, were increased (D7 and D14), and support time of three limbs was increased (D7). Moreover, significant changes were also observed in parameters describing fine motor functions such as: decreased hind limb toe clearance (D7), increased deviation of hip angle range of motion (D7), increased head movements (D14), decreased fore limb toe liftoff angle (D7), and decreased hind limb trajectory height profile (D14).

An overall gait analysis score was established to assess the AAV1/2-A53T-induced gait deficits in vehicle-treated AAV1/2-A53T mice as compared to AAV1/2-Null control group, with emphasis on left-right asymmetry. The overall gait score was determined by the discriminant vector which was constructed using PCA and by utilizing the PC score differences of the two groups (pooled from D7 and D14 vehicle treated groups). The data set used in PCA consisted of 76 selected parameters; all bilaterally determined parameters were expressed as the difference between the left and right sides. All parameters were normalized to standard scores. The discriminant vector bar graph (FIG. 6B) illustrates the combination of variables which best characterizes and captures the AAV1/2-A53T induced gait changes which can be interpreted as follows: The overall speed (stride time, distance, and speed) was slower and double support phase was increased especially in hindlimbs. Also, the proportion of diagonal support was decreased and support three and four (3 or 4 limbs simultaneously in ground contact) were increased. The most distinct left-right-asymmetries were seen in hip angle (max and range), forelimb toe clearance, hindlimb retraction, and in hind limb swing speeds.

Condensing all of these gait variables which are emphasized in the discriminant vector together, the overall gait analysis score shows highly significant AAV1/2-A53T-aSyn induced phenotype at both D7 and D14 vehicle treated groups (Unpaired t-test, AAV-Null versus AAV-A53T Vehicle; $p<0.0001$ (D7), $p<0.01$ (D14)).

Analysis of effects of early RTX treatment (D7) on AAV1/2-A53T induced motor deficits showed RTX dose-dependent recovery of motor functions, indicated by the shift in overall gait analysis score towards the AAV1/2-Null group. The recovery of overall gait score after RTX treatment with low and high dose was significantly improved as compared to AAV1/2-A53T Vehicle-treated control group (One-way ANOVA, p=0.0013 followed by Dunnett's test: p=0.0063 (RTX 0.04 μg), p=0.0011 (RTX 0.125 μg)), suggesting a beneficial treatment effect (FIG. 6A). Treatment effects of D14 groups were not statistically significant ($p>0.05$; One-way ANOVA). There was however a trend towards the AAV1/2-Null group in both RTX treated groups when compared to the AAV1/2-A53T Vehicle mice.

Next, we examined separate gait parameters that significantly recovered ($p<0.05$, Unpaired t-test) by RTX treatment that accounted for the difference in overall score. We observed changes in: stride time and hind limb stance time (D7 high dose), diagonal gait (D7 both doses) and support diagonal (D7 high dose), support three (D7 high dose), homolateral and homologous gait (D7 high dose), hip ROM (D7 both doses, D14 high dose) and hip ROM deviation (D7, high dose), minimum knee angle (D7 high dose), head rotation (D14, both doses), and single and double support (D7 high dose) in RTX treated groups as compared to the AAV-A53T Vehicle group. Similarly to the overall gait score, these observed RTX-induced differences in single gait parameters were in the direction of the AAV-Null "healthy" control group. Importantly, the observed efficacy of RTX in improvement of these parameters were mostly the same which were initially affected by AAV1/2-A53T delivery, indicating functional motor recovery of the animals.

Four mice from the D14 AAV-Null group were excluded from the gait analysis because their gait performance suggested spinal cord injury due to the intrathecal surgical operation. Also, two animals from the D14 AAV-A53T Vehicle group were excluded. Both of these animals had no signs of gait impairments, and the other was confirmed to have likely unsuccessful AAV1/2-A53T transduction as indicated by ipsilateral striatal dopamine concentration at the level of healthy animals.

The PCA of the gait parameters of D7 and D14 dosing groups using ten Varimax-rotated principal components is shown in FIG. 7. The heat map (shown on the right) illustrates the original parameters that differentially influence each of the ten principal components. Each column of heat map also shows how the parameters correlate: white color=positive correlation, gray color=negative correlation, black=no correlation. The PC scores PC #1-PC #10 of the fine motor tests are presented at the left (group mean+/−SEM). The PC scores correspond to the PCs shown in the heat map on the right. For example, PC #2 can be interpreted as "diagonal inter-limb coordination", including the increase in both the ILC Diagonal and Support Diagonal (diagonal, i.e., trotting cadence), and the decrease of other cadence types. The % in brackets behind the PCs on the top of each panel refer to the percentage of variation in the original data that is explained by the respective PC. #$p<0.05$, AAV-A53T Vehicle D14 versus AAV-Null Vehicle D14 (Unpaired t-test); ###$p<0.001$, AAV-A53T Vehicle D7 versus AAV-Null Vehicle D7 (Unpaired t-test); * $p<0.05$, ** $p<0.005$, AAV-A53T Vehicle D7 versus AAV-A53T RTX 0.125 μg D7. PC=principal component, ILC=interlimb coordination.

Discussion. In the present study, a Parkinson's disease-like state was first induced in C57Bl/6J male mice at 8 weeks of age by unilateral adenovirus vector (AAV) infusion to substantia nigra (SN) in the right hemisphere of the brain. Infusion of the vector aimed at overexpressing mutated human A53T-α-synuclein leading to the degeneration of nigral dopaminergic neurons and reduction of dopamine levels in the striatum. This has been shown to lead in Parkinson's disease-like symptoms including motor deficits. In order to control for the effects of the virus infusion per se, control groups of mice infused with AAV-Null (empty) vector were used. After 7 or 14 days of AAV-A53T mediated disease model induction, the mice were treated with vehicle or resiniferatoxin (RTX, 0.04 μg or 0.125 μg) by single intrathecal infusion at lumbar spinal cord area. AAV-Null-treated healthy control mice were treated with vehicle at day 7 or 14.

The study showed no significant adverse effects of intrathecal RTX administration at low or high dose. Mortalities (6 mice out of 110 lost) in the study were evenly dispersed between the groups—2 mice treated with vehicle included. Moreover, 3 of these mice died during anesthesia during or after administration. The rest of the mortalities were observed within 24 hours after intrathecal infusion. Monitoring of the mice revealed that these mice did not recover properly from the surgery indicated by lethargic and passive behavior. Because the mortalities were evenly spread between the vehicle and both RTX low and high dose groups, this was likely caused by the invasive surgical procedure and complications with anesthesia. No adverse effects were observed in the rest of the mice. Also, steady weight gain was observed similarly in vehicle and RTX treated groups during the study.

Analysis of fine motor skills was performed 7 weeks after AAV infusion and 6 or 5 weeks after treatment with RTX. AAV-A53T-mediated disease state was observed as highly significant differences between the AAV-Null and respective AAV-A53T Vehicle groups. Comparing the AAV-A53T Vehicle groups to the resiniferatoxin-treated groups revealed also significant treatment effect of RTX in the early (D7) treatment groups at both low and high dose as the RTX-treated groups were shifted towards the AAV-Null ("healthy") group. In groups treated with RTX 14 days after AAV-A53T infusion, there was a similar however statistically non-significant trend towards the respective AAV-Null group. When separating out individual parameters by principal component analysis, these gait rescuing effects were strongest in parameters related to inter-limb coordination and parameters indicating attempts to compensate asymmetric changes which showed as e.g. increased hip angle range. Also, gait cycle of the AAV-A53T Vehicle-treated mice had significantly more "jerking motion" indicating a less smooth gait typical for human PD. Asymmetric changes in gait are expected in mice that were infused with AAV-A53T unilaterally AAV-Null groups had similar levels of dopamine, DOPAC and HVA in ipsilateral and contralateral *striata* contrary to AAV-A53T infused mice that had significantly lower levels of dopamine and metabolites levels on the ipsilateral side treated with viral vectors with mutated A53T-α-synuclein. These results indicate that the disease model was induced successfully in both D7 and D14 groups. However, no significant effects of RTX treatment was shown when dopamine and its metabolites levels were compared between the AAV-A53T groups dosed with Vehicle and the corresponding groups treated with RTX. This suggests that the significant mitigating of gait impairments were transmitted through mechanisms not directly related to the nigrostriatal dopaminergic pathway. Neuroinflammation is known to play an important role in PD and its attenuation might be one possible explanation for the observed beneficial effects of RTX.

In conclusion, intrathecal administration of RTX 7 days after AAV-A53T model induction had a significant rescuing effect in C57Bl/6J male mice when motor skills were analyzed 7 weeks after AAV infusion. Similar statistically non-significant trending effect was observed in groups treated with RTX 14 days after AAV-A53T infusion. However, dopamine and metabolites levels analyzed from *striata* 8 weeks after model induction showed no significant treatment effect suggesting a mechanism of action not directly related to the nigrostriatal dopaminergic pathway. No significant adverse effects of RTX treatment were observed.

Example 2. Analysis of Gait Accounting for Left-Right Asymmetry

D7 fine motor gait analysis data from the study described above was reevaluated to determine how left-right asymmetry is manifested on kinematic parameters instead of assessing changes which occur bilaterally and that are captured in the "normal" overall gait score.

Typically, both the left and right sides of an animal are assessed for test parameters and the overall score and discriminant vector is based on the average of both the left and right-side values for a particular parameter. For example, the maximum hip angle is determined by the average of the left and right-side angle and it is similar in both AAV-Null Vehicle and AAV-A53T Vehicle groups. However, as shown in FIGS. 8A-8C when the left and right side measurements of the maximum hip angle were analyzed separately, the hip angle max of AAV-A53T Vehicle treated mice is smaller on the left side (FIG. 8A) than on the right side (FIG. 8B) when compared to AAV-Null mice. FIG. 8C shows the maximum left-right difference of hip angle is greatest in AAV-A53T Vehicle treated mice. Mice treated with AAV-A53T and 0.05 μg RTX (n=14) and with AAV-A53T and 0.124 μg RTX (n=14) showed a reduction in the maximum difference when compared to AAV-A53T- and Vehicle-treated mice.

Fine motor gait analysis was performed by creating a discriminant vector using the transformed data set, where left-right difference is used instead of the average of left and right. As shown in FIG. 9A, the bar length corresponds to the left-right asymmetry of a parameter which pronounced in the AAV-A53T vehicle group in comparison to the AAV-Null group. individual gait parameters used for the PCA analysis are shown for groups dosed on day 7. In FIG. 9B the left-right gait difference discriminant score shows a significant phenotype in the AAV-A53T vehicle group. Both groups treated with RTX showed significantly lower Discriminant Vector Scores compared to the AAV-A53T vehicle group ($p<0.05$, Unpaired t-test).

Figure 10F:
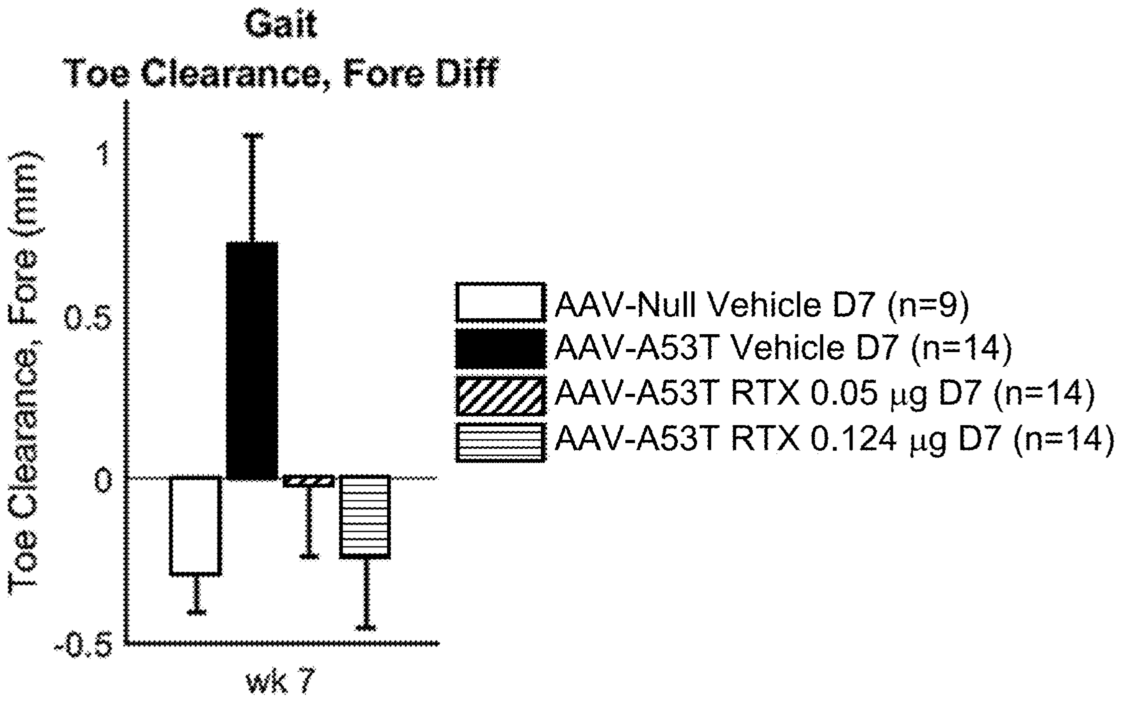

Left-right asymmetry was also analyzed for other gait parameters such as interlimb coordination, hip function, swing speeds, and forelimb to clearance. Left-right asymmetry manifested on diagonal interlimb coordination is shown in FIG. 10A-10C. Graphs of the percentage of diagonal interlimb coordination for the left side and for the right side are shown in FIGS. 10A and 10B respectively. The diagonal interlimb co-ordination is lower for the left side than the right side for the AAV-A53T vehicle group. The left-right difference is shown in FIG. 10C and reveals an RTX treatment effect as the mice in both the low and high RTX dose groups exhibit less of a a diagonal interlimb coordination difference that is in the range of the AAV-A53T Vehicle treated mice. The fore toe clearance parameter, an aspect of body posture and balance, is shown in FIG. 10D-10F. Left side, right side and left-right difference are shown in FIGS. 10D, 10E, and 10F, respectively. AAV-A53T Vehicle mice showed greater toe clearance on the left side (FIG. 10D) than on the right (FIG. 10E). The left-right difference graph (FIG. 10F) showed that both groups of RTX treated mice showed toe clearance similar to AAV-Null Vehicle mice and distinct from the AAV-A53T Vehicle group.

Fine motor skills were further evaluated by examining left-right asymmetry of the hindlimb peak swing speed and swing speed metric as shown in FIG. 11 A-11-F. The graphs of hindlimb peak swing speed (cm/s) for the left side and for the right side are shown in FIGS. 11A and 11B respectively. The peak swing speed left-right difference of both RTX treated groups is reduced compared to the AAV-A53T Vehicle D7 group as shown in FIG. 11C. The graphs of hindlimb swing speed (cm/s) for the left side and for the right side are shown in FIGS. 11D and 11E respectively. The left-right difference of both RTX treated groups is reduced compared to the AAV-A53T Vehicle D7 group as shown in FIG. 11E.

We claim:

1. A method for treating Parkinson's Disease (PD) comprising administering to a subject in need of treatment for PD an effective amount of Resiniferatoxin (RTX) intrathecally or intracisternally.

2. The method of claim 1, wherein the subject is an adult human.

3. The method of claim 1, wherein the RTX is administered in a dose of from about 0.1 μg to about 100 μg.

4. The method of claim 3, wherein the dose is from about 0.1 μg to about 1 μg, about 1 μg to about 5 μg, about 5 μg to about 10 μg, about 10 μg, to about 20 μg, about 20 μg to about 50 μg, or about 50 to about 100 μg.

5. The method of claim 1, wherein the method comprises intrathecal administration.

6. The method of claim 1, wherein the method comprises intracisternal administration.

7. The method of claim 1, wherein the RTX is administered in a pharmaceutical formulation comprising the RTX and a pharmaceutically acceptable carrier.

8. The method of claim 7, wherein the pharmaceutically acceptable carrier comprises water.

9. The method of claim 7, wherein the pharmaceutically acceptable carrier comprises saline.

10. The method of claim 7, wherein the RTX is present in the pharmaceutical formulation at a concentration ranging from 1 μg/ml to 100 μg/ml.

11. The method of claim 10, wherein the RTX is present in the pharmaceutical formulation at a concentration ranging from 1 μg/ml to 5 μg/ml, 5 μg/ml to 10 μg/ml, 10 μg/ml to 20 μg/ml, 20 μg/ml to 50 μg/ml, or 50 μg/ml to 100 μg/ml.

* * * * *